(12) United States Patent
Hilgier et al.

(10) Patent No.: US 12,377,076 B2
(45) Date of Patent: Aug. 5, 2025

(54) COMPOUNDS FOR TREATING LYMPHOMA OR A T-CELL MALIGNANT DISEASE

(71) Applicant: Purdue Pharma L.P., Stamford, CT (US)

(72) Inventors: Katarina Hilgier, Zurich (CH); Francisco Ibanez Lopez, Alicante (ES); Thomas Jorg Mehrling, Riehen (CH)

(73) Assignee: Purdue Pharma L.P., Stamford, CT (US)

( * ) Notice: Subject to any disclaimer, the term of this patent is extended or adjusted under 35 U.S.C. 154(b) by 1076 days.

(21) Appl. No.: 17/414,797

(22) PCT Filed: Dec. 18, 2019

(86) PCT No.: PCT/IB2019/061034
§ 371 (c)(1),
(2) Date: Jun. 16, 2021

(87) PCT Pub. No.: WO2020/128912
PCT Pub. Date: Jun. 25, 2020

(65) Prior Publication Data
US 2022/0016084 A1    Jan. 20, 2022

(30) Foreign Application Priority Data

Dec. 18, 2018 (GB) ...................... 1820643
Dec. 18, 2018 (GB) ...................... 1820645
(Continued)

(51) Int. Cl.
*A61K 31/4184* (2006.01)
*A61K 9/00* (2006.01)
(Continued)

(52) U.S. Cl.
CPC ........ *A61K 31/4184* (2013.01); *A61K 9/0019* (2013.01); *A61K 45/06* (2013.01);
(Continued)

(58) Field of Classification Search
CPC .. A61K 31/4184; A61K 9/0019; A61K 45/06; A61P 7/00; A61P 35/00
See application file for complete search history.

(56) References Cited

U.S. PATENT DOCUMENTS 4,522,811 A    6/1985   Eppstein et al.
5,134,127 A    7/1992   Stella et al.
(Continued)

FOREIGN PATENT DOCUMENTS

CL    0501-2003    3/2003
CL    2272-2005    9/2005
(Continued)

OTHER PUBLICATIONS

Conlan et al. (1991). Clinical significance of hematologic parameters in non-Hodgkin's lymphoma at diagnosis. Cancer, 67(5), 1389-1395. (Year: 1991).*
(Continued)

Primary Examiner — Joseph K McKane
Assistant Examiner — Ashli Ariana Chicks
(74) Attorney, Agent, or Firm — McCarter & English, LLP; Yu Lu

(57) ABSTRACT

The invention relates to tinostamustine for use in the treatment of lymphoma or a T-cell malignant disease. Tinostamustine may cause side effects when administered to a patient, and it is desirable to minimise such effects. The present invention defines an improved treatment, wherein the dose of tinostamustine administered is varied based on the patients platelet count.

18 Claims, 5 Drawing Sheets

(30) Foreign Application Priority Data

| | | | |
|---|---|---|---|
| Mar. 6, 2019 | (GB) | .................................... | 1903003 |
| Mar. 6, 2019 | (GB) | .................................... | 1903005 |
| Jun. 12, 2019 | (GB) | .................................... | 1908434 |
| Jun. 12, 2019 | (GB) | .................................... | 1908436 |

(51) Int. Cl.
   *A61K 45/06* (2006.01)
   *A61P 7/00* (2006.01)
   *A61P 35/00* (2006.01)
   *G16H 20/10* (2018.01)

(52) U.S. Cl.
   CPC ................. *A61P 7/00* (2018.01); *A61P 35/00* (2018.01); *G16H 20/10* (2018.01)

(56) References Cited

U.S. PATENT DOCUMENTS

| | | | |
|---|---|---|---|
| 5,376,645 | A | 12/1994 | Stella et al. |
| 5,571,534 | A | 11/1996 | Jalonen et al. |
| 5,874,418 | A | 2/1999 | Stella et al. |
| 6,046,177 | A | 4/2000 | Stella et al. |
| 6,087,367 | A | 7/2000 | Breslow et al. |
| 6,133,248 | A | 10/2000 | Stella |
| 6,214,852 | B1 | 4/2001 | Kim et al. |
| 6,407,079 | B1 | 6/2002 | Muller et al. |
| 8,461,350 | B2 | 6/2013 | Brittain et al. |
| 8,609,864 | B2 | 12/2013 | Chen et al. |
| 8,962,855 | B2 | 2/2015 | Chen et al. |
| 9,096,627 | B2 | 8/2015 | Chen et al. |
| 9,376,395 | B2 | 6/2016 | Chen et al. |
| RE46,144 | E | 9/2016 | Chen et al. |
| 9,889,147 | B2 | 2/2018 | Utku |
| 9,993,482 | B2 * | 6/2018 | Mehrling .............. A61K 31/553 |
| 10,118,901 | B2 | 11/2018 | Chen et al. |
| 10,406,138 | B2 * | 9/2019 | Mehrling ................ A61K 31/69 |
| 10,744,120 | B2 * | 8/2020 | Mehrling ................ A61P 43/00 |
| 11,266,631 | B2 * | 3/2022 | Mehrling .............. A61K 39/395 |
| 11,318,117 | B2 * | 5/2022 | Mehrling ................ A61P 35/04 |
| 11,413,276 | B2 * | 8/2022 | Mehrling .............. A61K 31/416 |
| 11,419,853 | B2 * | 8/2022 | Mehrling ................ A61P 25/00 |
| 11,541,038 | B2 * | 1/2023 | Mehrling ................ A61P 43/00 |
| 11,559,516 | B2 * | 1/2023 | Mehrling ................ A61P 25/00 |
| 11,576,899 | B2 | 2/2023 | Mehrling |
| 11,766,424 | B2 * | 9/2023 | Mehrling ........... A61K 47/6849 514/394 |
| 11,786,509 | B2 * | 10/2023 | Mehrling ........... A61K 31/4184 514/394 |
| 11,896,583 | B2 * | 2/2024 | Mehrling .............. A61K 31/337 |
| 11,918,558 | B2 * | 3/2024 | Mehrling ................ A61P 35/04 |
| 12,048,688 | B2 | 7/2024 | Mehrling et al. |
| 12,064,417 | B2 | 8/2024 | Mehrling et al. |
| 2002/0076409 | A1 | 6/2002 | March et al. |
| 2006/0079528 | A1 | 4/2006 | Finn et al. |
| 2006/0159713 | A1 | 7/2006 | Brittain et al. |
| 2008/0146556 | A1 | 6/2008 | Diebold et al. |
| 2010/0022512 | A1 | 1/2010 | Wisdom et al. |
| 2010/0216858 | A1 | 8/2010 | Popek et al. |
| 2011/0190363 | A1 | 8/2011 | Drager et al. |
| 2011/0269706 | A1 | 11/2011 | Chen et al. |
| 2011/0311624 | A1 | 12/2011 | Loury et al. |
| 2012/0289570 | A1 | 11/2012 | Lengyel et al. |
| 2013/0030237 | A1 | 1/2013 | Theuer |
| 2013/0209558 | A1 | 8/2013 | Patzak et al. |
| 2014/0303218 | A1 | 10/2014 | Chen et al. |
| 2015/0086551 | A1 | 3/2015 | Chen et al. |
| 2015/0231198 | A1 | 8/2015 | Carniti et al. |
| 2017/0095482 | A1 | 4/2017 | Mehrling |
| 2017/0151218 | A1 | 6/2017 | Mehrling et al. |
| 2017/0189382 | A1 | 7/2017 | Mehrling et al. |
| 2017/0296513 | A1 | 10/2017 | Mehrling et al. |
| 2018/0098969 | A1 | 4/2018 | Mehrling et al. |
| 2019/0343807 | A1 | 11/2019 | Mehrling et al. |
| 2020/0113870 | A1 | 4/2020 | Mehrling |
| 2020/0113871 | A1 | 4/2020 | Mehrling et al. |
| 2020/0230109 | A1 | 7/2020 | Mehrling |
| 2020/0261423 | A1 | 8/2020 | Mehrling |
| 2020/0397759 | A1 | 12/2020 | Mehrling et al. |
| 2021/0059989 | A1 | 3/2021 | Mehrling et al. |
| 2021/0346351 | A1 | 11/2021 | Mehrling et al. |
| 2022/0016085 | A1 | 1/2022 | Hilgier et al. |
| 2023/0049350 | A1 | 2/2023 | Mehrling et al. |
| 2023/0277507 | A1 | 9/2023 | Mehrling |
| 2024/0082220 | A1 | 3/2024 | Mehrling et al. |
| 2024/0139155 | A1 | 5/2024 | Mehrling |
| 2024/0252472 | A1 | 8/2024 | Diaz-Tejedor et al. |
| 2024/0261265 | A1 | 8/2024 | Mehrling |
| 2024/0316009 | A1 | 9/2024 | Mehrling et al. |

FOREIGN PATENT DOCUMENTS

| | | | |
|---|---|---|---|
| CL | 3232-2006 | 11/2006 | |
| CN | 1764648 A | 4/2006 | |
| CN | 101084876 A | 12/2007 | |
| CN | 101928234 A | 12/2010 | |
| CN | 102993102 A | 3/2013 | |
| DE | 34727 A1 | 12/1964 | |
| EP | 0717638 B1 | 3/2002 | |
| EP | 3148529 A1 | 4/2017 | |
| JP | 2007-531793 A | 11/2007 | |
| JP | 2012-515776 A | 7/2012 | |
| KR | 10-2001-0031896 A | 4/2001 | |
| WO | 1991/07950 A1 | 6/1991 | |
| WO | WO-1995/030442 A1 | 11/1995 | |
| WO | WO-2002/010161 A1 | 2/2002 | |
| WO | WO-2002/22577 A2 | 3/2002 | |
| WO | WO-2002/026696 A1 | 4/2002 | |
| WO | WO-2002/055017 A2 | 7/2002 | |
| WO | WO-2004/076386 A2 | 9/2004 | |
| WO | 2005/016859 A2 | 2/2005 | |
| WO | WO-2005/013958 A1 | 2/2005 | |
| WO | WO-2005/097747 A1 | 10/2005 | |
| WO | WO-2006/120456 A1 | 11/2006 | |
| WO | WO-2007/134169 A2 | 11/2007 | |
| WO | WO-2008/050125 A1 | 5/2008 | |
| WO | WO-2008/067027 A2 | 6/2008 | |
| WO | WO-2009/036016 A1 | 3/2009 | |
| WO | WO-2009/067453 A1 | 5/2009 | |
| WO | WO-2009/100045 A1 | 8/2009 | |
| WO | WO-2010/042568 A1 | 4/2010 | |
| WO | WO-2010/075542 A1 | 7/2010 | |
| WO | WO-2010/085377 A2 | 7/2010 | |
| WO | WO-2010/097700 A1 | 9/2010 | |
| WO | WO-2011/017448 A1 | 2/2011 | |
| WO | WO-2013/039488 A1 | 3/2013 | |
| WO | WO-2013040286 A2 * | 3/2013 | ............. A61K 31/16 |
| WO | WO-2013/113838 A1 | 8/2013 | |
| WO | WO-2015/085289 A1 | 6/2015 | |
| WO | WO-2015/180865 A1 | 12/2015 | |
| WO | WO-2015/181154 A1 | 12/2015 | |
| WO | WO-2015/181156 A1 | 12/2015 | |
| WO | WO-2015181157 A1 * | 12/2015 | ......... A61K 31/4184 |
| WO | WO-2016/087950 A1 | 6/2016 | |
| WO | WO-2017/067474 A1 | 4/2017 | |
| WO | 2018/229132 A1 | 12/2018 | |
| WO | 2018/229133 A1 | 12/2018 | |

OTHER PUBLICATIONS

Nair et al. A simple practice guide for dose conversion between animals and human. J Basic Clin Pharm. 2016;7(2):27-31. (Year: 2016).*

Sylman et al. A Temporal Examination of Platelet Counts as a Predictor of Prognosis in Lung, Prostate, and Colon Cancer Patients. Sci Rep 8, 6564 (2018). (Year: 2018).*

Advanced Accelerator Applications, Ongoing Clinical Studies with Advanced Accelerator Applications Pipeline Candidates. Retrieved online at: http://www.adacap.com/research-development/clinical-trials/. 6 pages, (2014).

Aguado Bueno et al., Preliminary Experience of the Spanish Compassionate Use Registry of Bendamustine in Patients with Relapsed

(56) References Cited

OTHER PUBLICATIONS and/or Refractory Multiple Myeloma. Blood. 2012;120(21), Abstract 4035.
Al-Ani et al., Changes in urinary metabolomic profile during relapsing renal vasculitis. Sci Rep. Dec. 1, 2016;6:38074. 11 pages.
Alfarouk et al., Resistance to cancer chemotherapy: failure in drug response from ADME to P-gp. Cancer Cell Int. Jul. 15, 2015;15:71.
American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).
Anastasia et al., Bendamustine for Hodgkin lymphoma patients failing autologous or autologous and allogeneic stem cell transplantation: a retrospective study of the Fondazione Italiana Linfomi. Br J Haematol. Jul. 2014;166(1):140-2.
Andersson et al., Discovery of novel drug sensitivities in T-PLL by high-throughput ex vivo drug testing and mutation profiling. Leukemia. Aug. 14, 2017. pp. 1-14.
Andersson et al., Primary T-Prolymphocytic Leukemia (T-PLL) Cells Are Sensitive to BCL-2 and HDAC Inhibitors: Results From High-Throughput Ex Vivo Drug Testing. Blood. 2013;122:3828. 6 pages.
Angelucci et al., Suberoylanilide hydroxamic acid partly reverses resistance to paclitaxel in human ovarian cancer cell lines. Gynecol Oncol. Dec. 2010;119(3):557-63.
Arun et al., The PARP inhibitor AZD2281 (Olaparib) induces autophagy/mitophagy in BRCA1 and BRCA2 mutant breast cancer cells. Int J Oncol. Jul. 2015;47(1):262-8.
Attal et al., Lenalidomide, Bortezomib, and Dexamethasone with Transplantation for Myeloma. The New England Journal of Medicine. Apr. 6, 2017;376:1311-1320.
Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.
Bachmann et al., Epigenetic silencing of BIM in glucocorticoid poor-responsive pediatric acute lymphoblastic leukemia, and its reversal by histone deacetylase inhibition. Blood. Oct. 21, 2010;116(16):3013-22.
Bagchi, Bendamustine for advanced sarcoma. Lancet Oncol. Aug. 2007;8(8):674.
Baker et al., Investigation of bendamustine HCL in a phase 2 study in women with resistant ovarian cancer. Invest New Drugs. Feb. 2013;31(1):160-6.
Balfour et al., Bendamustine. Drugs. 2001;61(5):631-8.
Barendsen et al., Inhibition of TPA-induced monocytic differentiation in THP-1 human monocytic leukemic cells by staurosporine, a potent protein kinase C inhibitor. Leuk Res. 1990;14(5):467-74.
Bender, Across the divide. The blood-brain barrier represents a formidable obstacle for cancer drugs. Nature. Sep. 27, 2018;561:S46-S47.
Berenson et al., Phase I/II trial assessing bendamustine plus bortezomib combination therapy for the treatment of patients with relapsed or refractory multiple myeloma. Br J Haematol. Feb. 2013;160(3):321-30.
Bernhard et al., Quality of life and quality-adjusted survival (Q-TWIST) in patients receiving dose-intensive or standard dose chemotherapy for high-risk primary breast cancer. Br J Cancer. Jan. 15, 2008;98(1):25-33.
Besse et al., The first in class, alkylator-histone-deacetylase-inhibitor fusion molecule EDO-S101 in combination with proteasome inhibitors induces highly synergistic pro-apoptotic signaling through UPR activation and suppression of c-Myc and BCL2 in multiple meyloma. ASH, 2016.
Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.
Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.
Biete et al., Whole abdominal radiotherapy in ovarian cancer. Rep Pract Oncol Radiother. Mar. 23, 2010;15(2):27-30.
Blattmann et al., Enhancement of radiation response in osteosarcoma and rhabdomyosarcoma cell lines by histone deacetylase inhibition. Int J Radiat Oncol Biol Phys. Sep. 1, 2010;78(1):237-45.
Bose et al., Histone deacetylase inhibitor (HDACI) mechanisms of action: emerging insights. Pharmacol Ther. Sep. 2014;143(3):323-36.
Botrugno et al., Molecular pathways: old drugs define new pathways: non-histone acetylation at the crossroads of the DNA damage response and autophagy. Clin Cancer Res. May 1, 2012;18(9):2436-42.
Braga et al., Crystal Polymorphism and Multiple Crystal Forms. Struct Bond. 2009;132:25-50.
Brewster et al., Cyclodextrins as pharmaceutical solubilizers. Adv Drug Deliv Rev. Jul. 30, 2007;59(7):645-66.
Bruce et al., Glioblastoma Multiforme Treatment & Management. Medscape. Retrieved online at: https://emedicine.medscape.com/article/283252-treatment. 20 pages. Jun. 14, 2017.
Buglio et al., Histone deacetylase inhibitors in Hodgkin lymphoma. Invest New Drugs. Dec. 2010;28 Suppl 1:S21-7.
Buglio et al., Vorinostat inhibits STAT6-mediated TH2 cytokine and TARC production and induces cell death in Hodgkin lymphoma cell lines. Blood. Aug. 15, 2008;112(4):1424-33.
Cai et al., Combination of bendamustine and entinostat synergistically inhibits proliferation of multiple myeloma cells via induction of apoptosis and DNA damage response. Cancer Lett. Jul. 28, 2013;335(2):343-50.
Cai et al., Discovery of 7-(4-(3-ethynylphenylamino)-7-methoxyquinazolin-6-yloxy)-N-hydroxyheptanamide (CUDc-101) as a potent multi-acting HDAC, EGFR, and HER2 inhibitor for the treatment of cancer. J Med Chem. Mar. 11, 2010;53(5):2000-9.
Cai et al., Solubilization of vorinostat by cyclodextrins. J Clin Pharm Ther. Oct. 2010;35(5):521-6.
Campos et al., Expression of nuclear receptor corepressors and class I histone deacetylases in astrocytic gliomas. Cancer Sci. Feb. 2011;102(2):387-92.
Chamberlain et al., Salvage therapy with bendamustine for methotrexate refractory recurrent primary CNS lymphoma: a retrospective case series. J Neurooncol. May 2014;118(1):155-62.
Chamberlain et al., Salvage therapy with single agent bendamustine for recurrent glioblastoma. J Neurooncol. Dec. 2011;105(3):523-30.
Chen et al., A 71-gene signature of TRAIL sensitivity in cancer cells. Mol Cancer Ther. Jan. 2012;11(1):34-44.
Chen et al., Dexamethasone and vorinostat cooperatively promote differentiation and apoptosis in Kasumi-1 leukemia cells through ubiquitination and degradation of AML1-ETO. Zhonghua Xue Ye Xue Za Zhi. Sep. 2013;34(9):741-4.
Chen et al., Discovery of a Novel, Efficient, and Scalable Route to Bendamustine Hydrochloride: The API in Treanda. Org Process Res Dev. 2011;15(5):1063-1072.
Chesi et al., Drug response in a genetically engineered mouse model of multiple myeloma is predictive of clinical efficacy. Blood. Jul. 12, 2012;120(2):376-85.
Chesi et al., Identification of Novel Therapeutic Targets in the Clinically Predictive Vk*MYC Mouse Model of Multple Myeloma. ASH, 2 pages. 2014.
Chesi et al., Identification of Novel Therapeutic Targets in the Clinically Predictive Vk*MYC Mouse Model of Multple Myeloma. Blood. 2014;124:415.
Chisholm et al., Emergence of drug tolerance in cancer cell populations: an evolutionary outcome of selection, nongenetic instability, and stress-induced adaptation. Cancer Res. Mar. 15, 2015;75(6):930-9.
Chiu et al., Suberoylanilide hydroxamic acid, an inhibitor of histone deacetylase, enhances radiosensitivity and suppresses lung metastasis in breast cancer in vitro and in vivo. PLoS One. Oct. 10, 2013;8(10):e76340. 12 pages.

(56) References Cited

OTHER PUBLICATIONS

Choi et al., Enhanced cytotoxic effect of radiation and temozolomide in malignant glioma cells: targeting PI3K-AKT-mTOR signaling, HSP90 and histone deacetylases. BMC Cancer. Jan. 13, 2014;14:17. 12 pages.

Chow et al., In vitro induction of apoptosis of neoplastic cells in low-grade non-Hodgkin's lymphomas using combinations of established cytotoxic drugs with bendamustine. Haematologica. May 2001;86(5):485-93.

Ciavatta et al., Epigenetic basis for aberrant upregulation of autoantigen genes in humans with ANCA vasculitis. J Clin Invest. Sep. 2010;120(9):3209-19.

Ciusani et al., Valproic acid increases the in vitro effects of nitrosureas on human glioma cell lines. Oncol Res. 2007;16(10):453-63.

ClinicalTrials.gov, A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies. Clinical Trials Identifier: NCT02576496, Oct. 14, 2015. 5 pages.

ClinicalTrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.

ClinicalTrials.gov, Phase 1 Trial of Dasatinib and Bendamustine in Chronic Lymphocytic Leukemia. ClinicalTrials Identifier: NCT00872976, Apr. 22, 2009. 3 pages.

ClinicalTrials.gov, Study of EDO-S101, A First-in-Class Alkylating HDACi Fusion Molecule, in Relapsed/Refractory Hematologic Malignancies. ClinicalTrials.gov Identifier: NTC02576496, 4 pages, Oct. 2015.

ClinicalTrials.gov, Study of the Safety, Pharmacokinetics and Efficacy of EDO-S101, in Patients With Advanced Solid TumorsClinical Trials Identifier: NCT03345485, Dec. 24, 2020. 12 pages.

Connors, Hodgkin lymphoma: special challenges and solutions. Hematol Oncol. Jun. 2015;33 Suppl 1:21-4.

Cooke et al., Spontaneous onset and transplant models of the Vk*MYC mouse show immunological sequelae comparable to human multiple myeloma. J Transl Med. Sep. 6, 2016;14:259. 12 pages.

Corazzelli et al., Efficacy and safety of bendamustine for the treatment of patients with recurring Hodgkin lymphoma. Br J Haematol. Jan. 2013;160(2):207-15.

Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Blood. 2015;126(23):2479. 7 pages.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1 page.

De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. ASH 57th Annual Meeting & Exposition. Abstract No. 2481. Dec. 5-8, 2015 [Downloaded from: [ttps://ash.confex.com/ash/2015/webprogram/Paper84797.html]. 2 pages.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. Blood. 2015;126:2481, 5 pages.

Deangelo et al., Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood. Dec. 1, 2006;108(12):3674-81.

Desouza et al., Has the survival of patients with glioblastoma changed over the years? Br J Cancer. Jan. 19, 2016;114(2):146-50.

Detich et al., Valproate induces replication-independent active DNA demethylation. J Biol Chem. Jul. 25, 2003;278(30):27586-92.

Diehl, The Evolution of Chemotherapy, Using the A-DAC Principle to Unlock New Treatment Options in Hodgkin Lymphoma. Mundipharma EDO Satellite Symposium, 10th International Symposium on Hodgkin Lymphoma, 6 pages, Oct. 23, 2016.

Dooley et al., Alkylating Histone Deacetylase Inhibitor Treatment in Animal Models of MPO-ANCA Vasculitis. Abstract TH-PO052. ASN, Kidney Week, Nov. 2, 2017, 2 pages.

Drogaris et al., Histone deacetylase inhibitors globally enhance h3/h4 tail acetylation without affecting h3 lysine 56 acetylation. Sci Rep. 2012;2:220. 12 pages.

Dohner et al., Diagnosis and management of acute myeloid leukemia in adults: recommendations from an international expert panel, on behalf of the European LeukemiaNet. Blood. Jan. 21, 2010;115(3):453-74.

Edoncology.com, The A-DAC Principle: A New Concept in Oncology Treatment. 3 pages, Sep. 2016.

EU Clinical Trials Register, EudraCT No. 2005-002051-41. 13 pages. Dec. 7, 2016.

EU Clinical Trials Register, EudraCT No. 2005-006083-57. 28 pages. Jun. 1, 2016.

Eurordis, Rare Diseases Europe, Why Research on Rare Diseases? Position Paper. Retrieved online at: www.eurordis.org. 14 pages. Oct. 2010.

Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.

Festuccia et al., Enhancement of radiosensitivity by the novel anticancer quinolone derivative vosaroxin in preclinical glioblastoma models. EJC, European Journal of Cancer. Dec. 2016;69(Suppl 1):S62. Abstract 174, Poster P145.

Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.

Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.

Formenti et al., Results of a phase I-II study of adjuvant concurrent carboplatin and accelerated radiotherapy for triple negative breast cancer. Oncoimmunology. Dec. 27, 2016;6(3):e1274479, 8 pages.

Frew et al., Enhancing the apoptotic and therapeutic effects of HDAC inhibitors. Cancer Lett. Aug. 8, 2009;280(2):125-33.

Furumai et al., Potent histone deacetylase inhibitors built from trichostatin A and cyclic tetrapeptide antibiotics including trapoxin. Proc Natl Acad Sci U S A. Jan. 2, 2001;98(1):87-92.

Geurink et al., Incorporation of non-natural amino acids improves cell permeability and potency of specific inhibitors of proteasome trypsin-like sites. J Med Chem. Feb. 14, 2013;56(3):1262-75.

Ghesquières et al., Clinical experience of bendamustine in relapsed or refractory Hodgkin lymphoma: a retrospective analysis of the French compassionate use program in 28 patients. Leuk Lymphoma. Nov. 2013;54(11):2399-404.

Gillis, HDAC Inhibition Appears to Sensitive Triple-Negative Breast Cancer Cells to Certain Treatments. Retrieved online at: https://www.onclive.com/conference-coverage/sabcs-2012/hdac-inhibition-appears-to-sensitize-triplenegative-breast-cancer-cells-to-certain-treatment, 2 pages, (2012).

Golub et al., Molecular classification of cancer: class discovery and class prediction by gene expression monitoring. Science. Oct. 15, 1999;286(5439):531-7.

(56) References Cited

OTHER PUBLICATIONS

Graham et al., T-cell prolymphocytic leukemia. Proc (Bayl Univ Med Cent). Jan. 2013;26(1):19-21.
Gravina et al., The novel CXCR4 antagonist, PRX177561, reduces tumor cell proliferation and accelerates cancer stem cell differentiation in glioblastoma preclinical models. Tumor Biology. Jun. 2017;1-17.
Greaves et al., Clonal evolution in cancer. Nature. Jan. 18, 2012;481(7381):306-13.
Griffith et al., A novel anti-cancer bifunctional platinum drug candidate with dual DNA binding and histone deacetylase inhibitory activity. Chem Commu (Camb). Nov. 28, 2009;(44):6735-7.
Griffith et al., Novel Platinum Pyridinehydroxamic Acid Complexes: Synthesis, Characterisation, X-ray Crystallographic Study of Nitric Oxide Related Properties. Polyhedron. 2007;26:4697-4706.
Groselj et al., Histone deacetylase inhibitors as radiosensitisers: effects on DNA damage signalling and repair. Br J Cancer. Mar. 5, 2013;108(4):748-54.
Hancock et al., HDAC inhibitor therapy in autoimmunity and transplantation. Ann Rheum Dis. Apr. 2012;71 Suppl 2:146-54.
Harrison et al., High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial. Blood. 2008;112, Abstract 3698. ASH Annual Meeting.
Hedgethorne et al., FORETINIB, c-Met and VEGFR-2 Inhibitor Oncolytic. Drugs of the Future. 2010;35(11):893-902.
Hegi et al., MGMT gene silencing and benefit from temozolomide in glioblastoma. N Engl J Med. Mar. 10, 2005;352(10):997-1003.
Her et al., Targeting DNA Double-strand Break Repair in Cancer Therapy. Journal of Molecular and Genetic Medicine. Dec. 31, 2015;9:e106, 1 page.
Herbaux et al., Bendamustine is effective in T-cell prolymphocytic leukaemia. Br J Haematol. Mar. 2015;168(6):916-9.
Herold et al., Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19). J Cancer Res Clin Oncol. Feb. 2006;132(2):105-12.
Herold et al., BOP versus COP in Advanced Low Grade Non-Hodgkin's Lymphomas—Results of a Randomized Multicenter Study. Blood. 1999;94:262b. Abstract 4382.
Hideshima et al., Mechanism of action of proteasome inhibitors and deacetylase inhibitors and the biological basis of synergy in multiple myeloma. Mol Cancer Ther. Nov. 2011;10(11):2034-42.
Hoffman, Brentuximab Vedotin Plus Bendamustine Active in Heavily Pretreated Hodgkin Lymphoma, ALCL. Cancer Therapy Advisor, Dec. 7, 2015. 2 pages. retreived online at: http://www.cancertherapyadvisor.com/ash-2015/hodgkin-lymphoma-alcl-brentuximab-vedotin-better-treatment-risk/article/458249/.
Hong et al., Complete Durable Response From Carboplatin and Olaparib in a Heavily Pretreated Triple-Negative Metastatic Breast Cancer With Germline BRCA2 and "BRCAness" Mutations. J Oncol Pract. Mar. 2016;12(3):270-2.
Howlader et al., Contributions of Subtypes of Non-Hodgkin Lymphoma to Mortality Trends. Cancer Epidemiol Biomarkers Prev. Jan. 2016;25(1):174-9.
Hummel et al., A pediatric phase 1 trial of vorinostat and temozolomide in relapsed or refractory primary brain or spinal cord tumors: a Children's Oncology Group phase 1 consortium study. Pediatr Blood Cancer. Sep. 2013;60(9):1452-9.
Ihle et al., HR23b expression is a potential predictive biomarker for HDAC inhibitor treatment in mesenchymal tumours and is associated with response to vorinostat. The Journal of Pathology: Clinical Research. 2016;2:59-71.
Jagannath et al., Bortezomib in combination with dexamethasone for the treatment of patients with relapsed and/or refractory multiple myeloma with less than optimal response to bortezomib alone. Haematologica. Jul. 2006;91(7):929-34.
Jawhari et al., In Vitro and In Vivo Preclinical Activity of EDO-S101 in Hodgkin Lymphoma. Haematologica. 2016;101(s5):6-7, Abstract P037.
Jennette et al., Pathogenesis of antineutrophil cytoplasmic autoantibody-mediated disease. Nat Rev Rheumatol. Aug. 2014;10(8):463-73.
Jiang et al., A mammalian functional-genetic approach to characterizing cancer therapeutics. Nature Chemical Biology. Feb. 2011;7:92-100.
Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.
Kalin et al., Creating zinc monkey wrenches in the treatment of epigenetic disorders. Curr Opin Chem Biol. Jun. 2009;13(3):263-71.
Kallenberg, Pathogenesis and treatment of ANCA-associated vasculitides. Clin Exp Rheumatol. Jul.-Aug. 2015;33(4 Suppl 92):S11-4.
Kallenberg, Pathogenesis of ANCA-associated vasculitides. Ann Rheum Dis. Mar. 2011;70 Suppl 1:i59-63.
Kalsi et al., The impact of low-grade toxicity in older people with cancer undergoing chemotherapy. Br J Cancer. Dec. 9, 2014;111(12):2224-8.
Kampa-Schittenhelm et al., Quizartinib (AC220) is a potent second generation class III tyrosine kinase inhibitor that displays a distinct inhibition profile against mutant-FLT3, -PDGFRA and -KIT isoforms. Molecular Cancer. 2013;12:19, 15 pages.
Kaufman et al., Lenalidomide. Bortezomib. and Dexamethasone (RVD) in Combination with Vorinostat as Front-Line Therapy for Patients with Multiple Myeloma (MM): Results of a Phase 1 Study. Blood. 2012;120, Abstract No. 336. 2 pages. ASH Annual Meeting.
Keating et al., Bendamustine. Nat Rev Drug Discov. Jun. 2008;7(6):473-4.
Khot et al., Panobinostat in lymphoid and myeloid malignancies. Expert Opin Investig Drugs. Sep. 2013;22(9):1211-23.
Kigawa, New strategy for overcoming resistance to chemotherapy of ovarian cancer. Yonago Acta Med. Jun. 2013;56(2):43-50.
Kim et al., Histone deacetylase inhibitors: molecular mechanisms of action and clinical trials as anti-cancer drugs. Am J Transl Res. Feb. 2011;3(2):166-79.
Knauf, Bendamustine in the treatment of chronic lymphocytic leukemia. Expert Rev Anticancer Ther. Feb. 2009;9(2):165-74.
Knittel et al., Two mouse models reveal an actionable PARP1 dependence in aggressive chronic lymphocytic leukemia. Nat Commun. Jul. 28, 2017;8(1):153. 13 pages.
Kollmannsberger et al., Phase II study of bendamustine in patients with relapsed or cisplatin-refractory germ cell cancer. Anticancer Drugs. Aug. 2000;11(7):535-9.
Kotzin et al., Reversal of nzb/nzw disease with total lymphoid irradiation. J Exp Med. Aug. 1, 1979;150(2):371-8.
Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.
Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.
Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.
Krause et al., Tyrosine kinases as targets for cancer therapy. N Engl J Med. Jul. 14, 2005;353(2):172-87.
Kumar et al., Histone deacetylase inhibitors induce cell death in supratentorial primitive neuroectodermal tumor cells. Oncol Rep. Nov. 2006;16(5):1047-52.
Lala et al., Role of nitric oxide in tumor progression: lessons from experimental tumors. Cancer Metastasis Rev. Mar. 1998;17(1):91-106.

(56) References Cited

OTHER PUBLICATIONS

Layman et al., Severe and prolonged lymphopenia observed in patients treated with bendamustine and erlotinib for metastatic triple negative breast cancer. Cancer Chemother Pharmacol. May 2013;71(5):1183-90.
Le Moigne et al., The p97 Inhibitor CB-5083 is a Unique Disrupter of Protein Homeostasis in Models of Multiple Myeloma. Molecular Cancer Therapeutics. Nov. 2017;16(11):2375-2386.
Lee et al., Phase I/Ib study of olaparib and carboplatin in BRCA1 or BRCA2 mutation-associated breast or ovarian cancer with biomarker analyses. J Natl Cancer Inst. May 19, 2014;106(6):dju089. 11 pages.
Lehmann et al., Refinement of Triple-Negative Breast Cancer Molecular Subtypes: Implications for Neoadjuvant Chemotherapy Selection. PLoS One. Jun. 16, 2016;11(6):e0157368, 22 pages.
Lentzsch et al., Combination of bendamustine, lenalidomide, and dexamethasone (BLD) in patients with relapsed or refractory multiple myeloma is feasible and highly effective: results of phase 1/2 open-label, dose escalation study. Blood. May 17, 2012;119(20):4608-13.
Leoni et al., Bendamustine (Treanda) displays a distinct pattern of cytotoxicity and unique mechanistic features compared with other alkylating agents. Clin Cancer Res. Jan. 1, 2008;14(1):309-17.
Leoni, Bendamustine: rescue of an effective antineoplastic agent from the mid-twentieth century. Semin Hematol. Apr. 2011;48 Suppl 1:S4-11.
Leung-Hagesteijn et al., Xbp1s-negative tumor B cells and pre-plasmablasts mediate therapeutic proteasome inhibitor resistance in multiple myeloma. Cancer Cell. Sep. 9, 2013;24(3):289-304.
Li et al., Pharmacokinetics of bendamustine in the central nervous system: chemoinformatic screening followed by validation in a murine model. MedChemComm. 2012;3:1526-1530.
Liby et al., Elevated and Deregulated Expression of HDAC3 in Human Astrocytic Glial Tumours. Folia Biologica (Praha). 2006;52:21-33.
Lin et al., Anti-rheumatic activities of histone deacetylase (HDAC) inhibitors in vivo in collagen-induced arthritis in rodents. Br J Pharmacol. Apr. 2007;150(7):862-72.
Lin et al., Treatment of Brain Metastases. J Clin Oncol. Oct. 20, 2015;33(30):3475-84.
Little et al., Experimental autoimmune vasculitis: an animal model of anti-neutrophil cytoplasmic autoantibody-associated systemic vasculitis. Am J Pathol. Apr. 2009;174(4):1212-20.
Little et al., Therapeutic effect of anti-TNF-alpha antibodies in an experimental model of anti-neutrophil cytoplasm antibody-associated systemic vasculitis. J Am Soc Nephrol. Jan. 2006;17(1):160-9.
Liu et al., A DNA/HDAC dual-targeting drug CY190602 with significantly enhanced anticancer potency. EMBO Mol Med. 12 pages, Published online: Mar. 9, 2015.
Liu et al., Effects of suberoylanilide hydroxamic acid (SAHA) combined with paclitaxel (PTX) on paclitaxel-resistant ovarian cancer cells and insights into the underlying mechanisms. Cancer Cell Int. Nov. 26, 2014;14(1):112, 11 pages.
Liu, Characterization of TCL1-Tg:P53- / -Mice that Resemble Human Chronic Lymphocytic Leukemia with 17P-Deletion. UT GSBS Thesis, Graduate School of Biomedical Sciences, Digital Commons@The Texas Medical Center, May 2013. 142 pages.
Loftsson et al., Historical Perspectives: Cyclodextrins and their pharmaceutical applications. International Journal of Pharmaceutics. 2007;329:1-11.
Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.
Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.
Lopez-Iglesias et al., Preclinical anti-myeloma activity of the alkylating-HDACi Fusion Molecule EDO-S101 Through DNA-damaging and HDACi Effects. Haematologica. 2014;99(s1):354-355, Abstract P942.
Lopez-Iglesias et al., Preclinical anti-myeloma activity of the alkylating-HDACi molecule EDO-S101 through DNA-damaging and HDACi effects. EDO, http://mundipharma-edo.com. Poster Jun. 1, 2014.
Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.
Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.
Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.
Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.
Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.
Ludwig et al., Bendamustine-bortezomib-dexamethasone is an active and well-tolerated regimen in patients with relapsed or refractory multiple myeloma. Blood. Feb. 13, 2014;123(7):985-91.
Marchion et al., Development of histone deacetylase inhibitors for cancer treatment. Expert Rev Anticancer Ther. Apr. 2007;7(4):583-98.
Marks, Discovery and development of SAHA as an anticancer agent. Oncogene. Feb. 26, 2007;26(9):1351-6.
Marmion et al., Hydroxamic Acids—An Intriguing Family of Enzyme Inhibitors and Biomedical Ligands. Eur J Inorg Chem. 2004(15):3003-3016.
McInnis et al., Dysregulation of autoantigen genes in ANCA-associated vasculitis involves alternative transcripts and new protein synthesis. J Am Soc Nephrol. Feb. 2015;26(2):390-9.
Meanwell, Synopsis of some recent tactical application of bioisosteres in drug design. J Med Chem. Apr. 28, 2011;54(8):2529-91.
Medline AN-NLM24103869, Chen et al., Dexamethasone and Vorinostat Cooperatively Promote Differentiation and Apoptosis in Kasumi-1 Leukemia Cells Through Ubiquitination and Degradation of AML1-ETO. 2 pages.
Medline/NLM AN: NLM24998648, 1 page.
Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.
Mehrling et al., Is there hope to treat glioblastoma effectively? CNS Oncol. 2015;4(6):377-9.
Mehrling et al., The Alkylating-HDAC Inhibition Fusion Principle: Taking Chemotherapy to the Next Level with the First in Class Molecule EDO-S101. Anticancer Agents Med Chem. 2016;16(1):20-8.
Mehrling, Chemotherapy is getting 'smarter'. Future Oncol. 2015;11(4):549-52.
Mehrling, First in human clinical trails to commence Q3 2015. Mundipharma EDO GmbH. Retrieved online at: http://mundipharma-edo.com. Jul. 31, 2015. 2 pages.
Mehrling, First-in-human clinical trial of its lead compound, EDO-S101. Mundipharma EDO GmbH. Retrieved online at: http://mundipharma-edo.com. May 31, 2016. 2 pages.
Mehrling, Fusion Therapy, a New Approach to Combining Treatments. Drug Discovery World. 2016;71-76.
Mehrling, Mundipharma EDO GmbH Announces FDA Investigational New Drug Approval of its First anti-Cancer Compound, EDO-S101, for the Treatment of Patients with Relapsed/Refractory Haematologic Malignancies and Solid Tumours. EDO, http://mundipharma-edo.com/2015/07/31/mundipharma-edo-gmbh-announces-fda-investigational-new-drug-approval-of-its-first-anti-

(56) References Cited

OTHER PUBLICATIONS cancer-compound-edo-s101-for-the-treatment-of-patients-with-relapsedrefractory-haematologic-malignancies-and-s/. 2 pages, Jul. 31, 2015.

Mehrling, Mundipharma EDO GmbH announces first-in-human clinical trial of its lead compound, EDO-S101. EDO, http://mundipharma-edo.com/2016/07/20/mundipharma-edo-gmbh-announces-first-in-human-clinical-trial-of-lead-compound-edo-s101/. 2 pages, May 31, 2016.

Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.

Miller et al., Histone deacetylase inhibitors. J Med Chem. Nov. 20, 2003;46(24):5097-116.

Min et al., Histone deacetylase inhibitor, suberoylanilide hydroxamic acid (SAHA), enhances anti-tumor effects of the poly (ADP-ribose) polymerase (PARP) inhibitor olaparib in triple- negative breast cancer cells. Breast Cancer Res. Mar. 7, 2015;17:33, 13 pages.

Minucci et al., Histone deacetylase inhibitors and the promise of epigenetic (and more) treatments for cancer. Nat Rev Cancer. Jan. 2006;6(1):38-51.

Mishra et al., Histone deacetylase inhibitors modulate renal disease in the MRL-Ipr/Ipr mouse. J Clin Invest. Feb. 2003;111(4):539-52.

Moosman et al., Weekly treatment with a combination of bortezomib and bendamustine in relapsed or refractory indolent non-Hodgkin lymphoma. Leuk Lymphoma. Jan. 2010;51(1):149-52.

Moradei et al., Histone deacetylase inhibitors: latest developments, trends and prospects. Curr Med Chem Anticancer Agents. Sep. 2005;5(5):529-60.

Moreau et al., Phase 1b Dose Escalation Study of Oral Quisinostat, a Histone Deacetylase Inhibitor (HDACi), In Combination With Velcade (Bortezomib) and Dexamethasone For Patients With Relapsed Multiple Myeloma (MM). Blood. Nov. 15, 2013;122(21):1932.

Moreau et al., Proteasome inhibitors in multiple myeloma: 10 years later. Blood. Aug. 2, 2012;120(5):947-59.

Moscovitch et al., Successful treatment of autoimmune manifestations in MRL/l and MRL/n mice using total lymphoid irradiation (TLI). Exp Mol Pathol. Feb. 1983;38(1):33-47.

Moskowitz et al., Phase II study of bendamustine in relapsed and refractory Hodgkin lymphoma. J Clin Oncol. Feb. 1, 2013;31(4):456-60.

Moskowitz, Bendamustine: a bridge to longer term solutions in heavily treated Hodgkin lymphoma. Leuk Lymphoma. Nov. 2013;54(11):2339-40.

MRF, Melanoma Research Foundation, Melanoma Central Nervous System Metastases, Current Approaches, Challenges and Opportunities. 5 pages (2015).

Munakata et al., The discovery and the development of bendamustine for the treatment of non-Hodgkin lymphoma. Expert Opin Drug Discov. Nov. 2016;11(11):1123-1130.

Munker et al., Activity of Tyrosine Kinase Inhibitors in Multiple Myeloma. Blood. 2007;110(11):274B, Abstract 4804.

National Institute of Health, Cancer. MedlinePlus. Retrieved online at: http://www.nlm.nih.gov/medlineplus/cancer.html. 10 pages. Apr. 16, 2007.

O'donnell et al., Cancer pharmacoethnicity: ethnic differences in susceptibility to the effects of chemotherapy. Clin Cancer Res. Aug. 1, 2009;15(15):4806-14.

O'reilly et al., Urinary Soluble CD163 in Active Renal Vasculitis. J Am Soc Nephrol. Sep. 2016;27(9):2906-16.

Ocio et al., Deacetylase Inhibition in Haematological Malignancies— Advanced T-cell Lymphoma, Hodgkin's Lymphoma, Multiple Myeloma, Acute Myelogenous Leukaemia and Myelodysplastic Syndrome. European Haematology. 2010;4:47-50.

Ocio et al., In vitro and in vivo rationale for the triple combination of panobinostat (LBH589) and dexamethasone with either bortezomib or lenalidomide in multiple myeloma. Haematologica. May 2010;95(5):794-803.

Ocio et al., Phase I study of plitidepsin in combination with bortezomib and dexamethasone in patients with relapsed and/or refractory multiple myeloma. Journal of Clinical Oncology. 2016;34:Abstract 8006, 1 page.

Ocio et al., Triple Combinations of the HDAC Inhibitor Panobinostat (LBH589) Plus Dexamethasone with Either Lenalidomide or Bortezomib are Highly Effective in a Multiple Myeloma Mouse Model. Blood. 2007;110:Abstract 1514. ASH Annual Meeting.

Ocio, Epigenetic regulation and HAC inhibitors, Still a role for these agents in MM? Institute of Biomedical Research of Salamanca, University of Salamanca, Cancer Research Center, Slideshow. 32 pages, (2016).

Offidani et al., Efficacy and tolerability of bendamustine, bortezomib and dexamethasone in patients with relapsed-refractory multiple myeloma: a phase II study. Blood Cancer J. Nov. 22, 2013;3:e162.

Ogura et al., A multicentre phase II study of vorinostat in patients with relapsed or refractory indolent B-cell non-Hodgkin lymphoma and mantle cell lymphoma. Br J Haematol. Jun. 2014;165(6):768-76.

Ol et al., Synergistic induction of NY-ESO-1 antigen expression by a novel histone deacetylase inhibitor, valproic acid, with 5-aza-2'-deoxycytidine in glioma cells. J Neurooncol. Mar. 2009;92(1):15-22.

Oken et al., Toxicity and response criteria of the Eastern Cooperative Oncology Group. Am J Clin Oncol. Dec. 1982;5(6):649-55.

Oriol et al., Outcome after relapse of acute lymphoblastic leukemia in adult patients included in four consecutive risk-adapted trials by the PETHEMA Study Group. Haematologica. Apr. 2010;95(4):589-596.

Paris et al., Histone deacetylase inhibitors: from bench to clinic. J Med Chem. Mar. 27, 2008;51(6):1505-29.

Phan et al., An update on ethnic differences in drug metabolism and toxicity from anti-cancer drugs. Expert Opin Drug Metab Toxicol. Nov. 2011;7(11):1395-410.

Phiel et al., Histone deacetylase is a direct target of valproic acid, a potent anticonvulsant, mood stabilizer, and teratogen. J Biol Chem. Sep. 28, 2001;276(39):36734-41.

Pitha et al., Parenteral hydroxypropyl cyclodextrins: intravenous and intracerebral administration of lipophiles. J Pharm Sci. Jun. 1994;83(6):833-7.

Poenisch et al., Bendamustine/Prednisone Versus Melphalane/ Prednisone in the Primary Treatment of Multiple Myeloma: an Updated Analysis of the 94BP01 Protocol. Blood. 2000;96(Suppl 1:759a), Abstract 3284, Poster Board Session 748-111.

Puetzer et al., Towards novel strategies of targeting specific vulnerabilities of T-PLL cells. AACR Annual Meeting. Jul. 2017;77(Suppl 13), Abstract 1372.

Pñnisch et al., Combined bendamustine, prednisone and bortezomib (BPV) in patients with relapsed or refractory multiple myeloma. J Cancer Res Clin Oncol. Mar. 2013;139(3):499-508.

Pönisch et al., Treatment of bendamustine and prednisone in patients with newly diagnosed multiple myeloma results in superior complete response rate, prolonged time to treatment failure and improved quality of life compared to treatment with melphalan and prednisone—a randomized phase III study of the East German Study Group of Hematology and Oncology (OSHO). J Cancer Res Clin Oncol. Apr. 2006;132(4):205-12.

Qian et al., Activity of PXD101, a histone deacetylase inhibitor, in preclinical ovarian cancer studies. Mol Cancer Ther. Aug. 2006;5(8):2086-95.

Rajewski et al., Preliminary safety evaluation of parenterally administered sulfoalkyl ether beta-cyclodextrin derivatives. J Pharm Sci. Aug. 1995;84(8):927-32.

Rang et al., Glucocorticoids. Rang and Dale's Pharmacology, Sixth Edition. Elsevier, Limited, 3 pages, (2007).

Rang et al., Rang and Dale's Pharmacology, Sixth Edition. Churchill Livingstone Elsevier. Chapter 51, p. 729, (2007).

Rasheed et al., Histone deacetylase inhibitors in cancer therapy. Expert Opin Investig Drugs. May 2007;16(5):659-78.

Rasschaert et al., A phase I study of bendamustine hydrochloride administered day 1+2 every 3 weeks in patients with solid tumours. Br J Cancer. Jun. 4, 2007;96(11):1692-8.

(56) References Cited

OTHER PUBLICATIONS

Rasschaert et al., A phase I study of bendamustine hydrochloride administered once every 3 weeks in patients with solid tumors. Anticancer Drugs. Jun. 2007;18(5):587-95.
Reagan-Shaw et al., Dose translation from animal to human studies revisited. FASEB J. Mar. 2008;22(3):659-61.
Regna et al., HDAC expression and activity is upregulated in diseased lupus-prone mice. Int Immunopharmacol. Dec. 2015;29(2):494-503.
Reilly et al., Modulation of renal disease in MRL/lpr mice by suberoylanilide hydroxamic acid. J Immunol. Sep. 15, 2004;173(6):4171-8.
Rengstl et al., Small and big Hodgkin-Reed-Sternberg cells of Hodgkin lymphoma cell lines L-428 and L-1236 lack consistent differences in gene expression profiles and are capable to reconstitute each other. PLoS One. May 15, 2017;12(5):e0177378.
Richardson et al., PANORAMA 2: panobinostat in combination with bortezomib and dexamethasone in patients with relapsed and bortezomib-refractory myeloma. Blood. Oct. 3, 2013;122(14):2331-7.
Rodriguez-Tenreiro Y Sanchez, Hydrogels of Cyclodextrin Co-crosslinked and Interpenetrated for Controlled Drug Release. University of Santiago de Compostela, School of Pharmacy. pp. 29-32, (2006).
Ryu et al., Valproic acid downregulates the expression of MGMT and sensitizes temozolomide-resistant glioma cells. J Biomed Biotechnol. 2012;2012:987495. 9 pages.
Sampson et al., Vorinostat Enhances Cytotoxicity of SN-38 and Temozolomide in Ewing Sarcoma Cells and Activates STAT3/AKT/MAPK Pathways. PLoS One. Nov. 16, 2015;10(11):e0142704, 19 pages.
Sanchez et al., Anti-Myeloma Effects of Carfilzomib with Cyclophosphamide (CY) or Bendamustine (Ben). Blood. 2012;120(21), Abstract 2952. 54th ASH Annual Meeting adn Exposition.
Santacruz et al., The prognostic impact of minimal residual disease in patients with chronic lymphocytic leukemia requiring first-line therapy. Haematologica. May 2014;99(5):873-80.
Sarkaria et al., Mechanisms of chemoresistance to alkylating agents in malignant glioma. Clin Cancer Res. May 15, 2008;14(10):2900-8.
Saulnier et al., An Efficient Method for the Synthesis of Guanidino Prodrugs. Bioorganic & Medicinal Chemistry Letters. 1994;4(16):1985-1990.
Sawas et al., The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience. Blood. 2015;126:586.
Schöffski et al., Repeated administration of short infusions of bendamustine: a phase I study in patients with advanced progressive solid tumours. J Cancer Res Clin Oncol. Jan. 2000;126(1):41-7.
Schöffski et al., Weekly administration of bendamustine: a phase I study in patients with advanced progressive solid tumours. Ann Oncol. Jun. 2000;11(6):729-34.
Shah et al., Comprehensive analysis of MGMT promoter methylation: correlation with MGMT expression and clinical response in GBM. PLoS One. Jan. 7, 2011;6(1):e16146.
Shipley et al., Acute myelogenous leukemia. Exp Hematol. Jun. 2009;37(6):649-58.
Simon, Optimal two-stage designs for phase II clinical trials. Control Clin Trials. Mar. 1989;10(1):1-10.
Song et al., Increased expression of histone deacetylase 2 is found in human gastric cancer. APMIS. 2005;113:264-8.
Stiborová et al., The synergistic effects of DNA-targeted chemotherapeutics and histone deacetylase inhibitors as therapeutic strategies for cancer treatment. Curr Med Chem. 2012;19(25):4218-38.
Storer, Design and analysis of phase I clinical trials. Biometrics. Sep. 1989;45(3):925-37.
Sturn et al., Genesis: cluster analysis of microarray data. Bioinformatics. Jan. 2002;18(1):207-8.
Tago et al., Repeated 0.5-Gy gamma irradiation attenuates autoimmune disease in MRL-lpr/lpr mice with suppression of CD3+CD4-CD8-B220+ T-cell proliferation and with up- regulation of CD4+CD25+Foxp3+ regulatory T cells. Radiat Res. Jan. 2008;169(1):59-66.
Takai et al., Human ovarian carcinoma cells: histone deacetylase inhibitors exhibit antiproliferative activity and potently induce apoptosis. Cancer. Dec. 15, 2004;101(12):2760-70.
Tesar et al., Limitations of standard immunosuppressive treatment in ANCA-associated vasculitis and lupus nephritis. Nephron Clin Pract. 2014; 128(3-4):205-15.
Thurn et al., Rational therapeutic combinations with histone deacetylase inhibitors for the treatment of cancer. Future Oncol. Feb. 2011;7(2):263-83.
Topalian et al., Immune checkpoint blockade: a common denominator approach to cancer therapy. Cancer Cell. Apr. 13, 2015;27(4):450-61.
Trivedi et al., Management of Chemotherapy-Induced Peripheral Neuropathy. American Journal of Hematology / Oncology. Jan. 2015;11(1):4-10.
Tsai et al., Valproic Acid Enhanced Temozolomide-Induced Anticancer Activity in Human Glioma Through the p53-PUMA Apoptosis Pathway. Front Oncol. Oct. 1, 2021;11:722754, 13 pages.
Tutt et al., Oral poly(ADP-ribose) polymerase inhibitor olaparib in patients with BRCA1 or BRCA2 mutations and advanced breast cancer: a proof-of-concept trial. Lancet. Jul. 24, 2010;376(9737):235-44.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Van Krieken, New developments in the pathology of malignant lymphoma. A review of the literature published from Jan.-Apr. 2016. J Hematop. Jun. 13, 2016;9(2):73-83.
Viel et al., Optimizing glioblastoma temozolomide chemotherapy employing lentiviral-based anti-MGMT shRNA technology. Mol Ther. Mar. 2013;21(3):570-9.
Vippagunta et al., Crystalline Solids. Advanced Drug Delivery Reviews. 2001;48:3-26.
Vlachostergios et al., Bortezomib downregulates MGMT expression in T98G glioblastoma cells. Cell Mol Neurobiol. Apr. 2013;33(3):313-8.
Vlachostergios et al., Bortezomib overcomes MGMT-related resistance of glioblastoma cell lines to temozolomide in a schedule-dependent manner. Invest New Drugs. Oct. 2013;31(5):1169-81.
Von Tresckow et al., An update on emerging drugs for Hodgkin lymphoma. Expert Opin Emerg Drugs. Jun. 2014;19(2):215-24.
Vyas et al., Cyclodextrin based novel drug delivery systems. J Incl Phenom Macrocycl Chem. 2008;62:23-42.
Wang et al., Effect of histone deacetylase inhibitor NL101 on rat neurons. Zhejiang Da Xue Bao Yi Xue Ban. May 2014;43(3):265-272. Abstract Only. 2 pages.
Wang et al., Independent validation of a model using cell line chemosensitivity to predict response to therapy. J Natl Cancer Inst. Sep. 4, 2013;105(17):1284-91.
Wang et al., Phase 1 trial of linifanib (ABT-869) in patients with refractory or relapsed acute myeloid leukemia. Leuk Lymphoma. Aug. 2012;53(8):1543-51.
Wang et al., Toward selective histone deacetylase inhibitor design: homology modeling, docking studies, and molecular dynamics simulations of human class I histone deacetylases. J Med Chem. Nov. 3, 2005;48(22):6936-47.
Watanabe et al., Modulation of renal disease in MRL/lpr mice genetically deficient in the alternative complement pathway factor B. J Immunol. Jan. 15, 2000;164(2):786-94.
Weil et al., Breast cancer metastasis to the central nervous system. Am J Pathol. Oct. 2005;167(4):913-20.
Wiegmans et al., Differences in Expression of Key DNA Damage Repair Genes after Epigenetic-Induced BRCAness Dictate Synthetic Lethality with PARP1 Inhibition. Mol Cancer Ther. Oct. 2015;14(10):2321-31.

(56) References Cited

OTHER PUBLICATIONS

Wikipedia, Triple-negative breast cancer. Retrieved online at: https://en.wikipedia.org/wiki/Triple-negative_breast_cancer. 7 pages, Feb. 20, 2017.

Wilson et al., Histone deacetylase 3 (HDAC3) and other class I HDACs regulate colon cell maturation and p21 expression and are deregulated in human colon cancer. J Biol Chem. May 12, 2006;281(19):13548-58.

Wilson et al., Relationship of p53, bcl-2, and tumor proliferation to clinical drug resistance in non-Hodgkin's lymphomas. Blood. Jan. 15, 1997;89(2):601-9.

Witzel et al., Long-term tumor remission under trastuzumab treatment for HER2 positive metastatic breast cancer—results from the HER-OS patient registry. BMC Cancer. Nov. 4, 2014;14:806. 7 pages.

Xiao et al., Antineutrophil cytoplasmic autoantibodies specific for myeloperoxidase cause glomerulonephritis and vasculitis in mice. J Clin Invest. Oct. 2002;110(7):955-63.

Xie et al., Quantitative structure-activity relationship study of histone deacetylase inhibitors. Curr Med Chem Anticancer Agents. May 2004;4(3):273-99.

Yan et al., Synergistic Inhibition of Tumor Growth and Overcoming Chemo-Resistance by Simultaneously Targeting Key Components in DNA Damage/Repair, Epigenetic, and Putative Cancer Stem Cell Signaling Pathways Using Novel Dual-Functional DNA-Alkylating/HDAC Inhibitor and Tumor Suppressor Gene Nanoparticles in Cancer Research. Cancer Research. Apr. 15, 2012;72(8, Suppl. 1) Proceedings: AACR 103rd Annual Meeting. Abstract 2741. 2 pages.

Yardley, Drug resistance and the role of combination chemotherapy in improving patient outcomes. Int J Breast Cancer. 2013;2013:137414. 15 pages.

Zaja et al., Bendamustine salvage therapy for T cell neoplasms. Ann Hematol. Sep. 2013;92(9):1249-54.

Zhang et al., A novel suberoylanilide hydroxamic acid histone deacetylase inhibitor derivative, N25, exhibiting improved antitumor activity in both human U251 and H460 cells. Asian Pac J Cancer Prev. 2014;15(10):4331-8.

Zhao et al., Comparison of methods for evaluating drug-drug interaction. Front Biosci (Elite Ed). Jan. 1, 2010;2:241-9.

Zhu et al., Histone deacetylase 3 implicated in the pathogenesis of children glioma by promoting glioma cell proliferation and migration. Brain Res. Jul. 3, 2013;1520:15-22.

Zinzani et al., Brentuximab Vedotin in Transplant-Naïve Relapsed/Refractory Hodgkin Lymphoma: Experience in 30 Patients. Oncologist. Dec. 2015;20(12):1413-6.

Zinzani et al., Dose Escalation of Tinostamustine in Patients with Relapsed/Refractory (R/R) Lymphoid Malignancies. Retrieved online at: https://library.ehaweb.org/eha/2019/24th/266100/delphine.remmy.dose.escalation.of.tinostamustine.in.patients.with.relapsed.html?f=listing-3*browseby=8*sortby=1*media=1. 1 page, poster presentation. Jun. 1, 2019.

Zulkowski et al., Regression of brain metastases from breast carcinoma after chemotherapy with bendamustine. J Cancer Res Clin Oncol. Feb. 2002;128(2):111-3.

U.S. Appl. No. 13/143,155, filed Jul. 1, 2011, U.S. Pat. No. 8,609,864, Issued.
U.S. Appl. No. 14/212,765, filed Mar. 25, 2021, 2021-0346351, Published.
U.S. Appl. No. 15/314,172, filed Nov. 26, 2016, 2017-0189382, Published.
U.S. Appl. No. 16/994,154, filed Aug. 14, 2020, 2021-0059989, Published.
U.S. Appl. No. 16/341,089, filed Apr. 11, 2019, 2020-0397759, Published.
U.S. Appl. No. 16/621,885, filed Dec. 12, 2019, 2020-0113870, Published.
U.S. Appl. No. 16/621,893, filed Dec. 12, 2019, 2020-0261423, Published.
U.S. Appl. No. 16/621,896, filed Dec. 12, 2019, 2020-0230109, Allowed.
U.S. Appl. No. 16/621,898, filed Dec. 12, 2019, 2020-0113871, Allowed.
U.S. Appl. No. 17/414,806, filed Jun. 16, 2021, Pending.
U.S. Appl. No. 13/143,155, filed Jul. 1, 20211, U.S. Pat. No. 8,609,864, Issued.
U.S. Appl. No. 14/075,145, filed Nov. 8, 2013, U.S. Pat. No. 9,096,627, Issued.
U.S. Appl. No. 14/972,750, filed Dec. 17, 2015, Re. 46,144, Issued.
U.S. Appl. No. 14/345,562, filed Nov. 3, 2014, U.S. Pat. No. 9,376,395, Issued.
U.S. Appl. No. 14/374,995, filed Jul. 28, 2014, U.S. Pat. No. 10,118,901, Issued.
U.S. Appl. No. 15/290,546, filed Oct. 11, 2016, 2018-0098969, Abandoned.
U.S. Appl. No. 15/314,162, filed Nov. 28, 2016, 2017-0151218, Abandoned.
U.S. Appl. No. 15/985,097, filed May 21, 2018, U.S. Pat. No. 10,406,138, Issued.
U.S. Appl. No. 16/517,936, filed Jul. 22, 2016, 2019-034807, Abandoned.
U.S. Appl. No. 14/212,765, filed Mar. 25, 2021, U.S. Pat. No. 11,559,516, Issued.
U.S. Appl. No. 18/086,958, filed Dec. 22, 2022, U.S. Pat. No. 12,048,688, Issued.
U.S. Appl. No. 18/743,233, filed Jun. 14, 2024, Pending.
U.S. Appl. No. 15/314,167, filed Nov. 28, 2016, U.S. Pat. No. 9,993,482, Abandoned.
U.S. Appl. No. 18/654,296, filed May 3, 2024, Pending.
U.S. Appl. No. 15/314,172, filed Nov. 28, 2016, U.S. Pat. No. 11,419,853, Issued.
U.S. Appl. No. 17/874,621, filed Jul. 27, 2022, 2023-0049350, Published.
U.S. Appl. No. 15/314,180, filed Nov. 28, 2016, U.S. Pat. No. 10,744,120, Issued.
U.S. Appl. No. 16/983,458, filed Aug. 3, 2020, Abandoned.
U.S. Appl. No. 16/994,154, filed Aug. 14, 2020, U.S. Pat. No. 11,541,038, Issued.
U.S. Appl. No. 18/083,651, filed Dec. 19, 2022, U.S. Pat. No. 12,064,417, Issued.
U.S. Appl. No. 18/775,245, filed Jul. 17, 2024, Pending.
U.S. Appl. No. 16/341,089, filed Apr. 11, 2019, U.S. Pat. No. 11,266,631, Issued.
U.S. Appl. No. 17/679,308, filed Feb. 24, 2022, U.S. Pat. No. 11,766,424, Issued.
U.S. Appl. No. 18/446,522, filed Aug. 9, 2023, 2024-0082220, Published.
U.S. Appl. No. 16/621,885, filed Dec. 12, 2019, U.S. Pat. No. 11,559,516, Issued.
U.S. Appl. No. 18/108,736, filed Feb. 13, 2023, 2023-0277507, Published.
U.S. Appl. No. 16/621,893, filed Dec. 12, 2019, U.S. Pat. No. 11,896,583, Issued.
U.S. Appl. No. 18/404,810, filed Jan. 4, 2024, 2024-0261265, Published.
U.S. Appl. No. 16/621,896, filed Dec. 12, 2019, U.S. Pat. No. 11,413,276, Issued.
U.S. Appl. No. 17/885,696, filed Aug. 11, 2022, U.S. Pat. No. 11,786,509, Issued.
U.S. Appl. No. 18/244,913, filed Sep. 12, 2023, 2024-0139155, Published.
U.S. Appl. No. 16/621,898, filed Dec. 12, 2019, U.S. Pat. No. 11,318,117, Issued.
U.S. Appl. No. 17/730,276, filed Apr. 27, 2022, U.S. Pat. No. 11,918,558, Issued.
U.S. Appl. No. 18/422,118, filed Jan. 25, 2024, 2024-0316009, Published.
U.S. Appl. No. 17/414,806, filed Jun. 16, 2021, 2022-0016085, Published.
U.S. Appl. No. 18/420,883, filed Jan. 24, 2024, 2024-0252472, Published.

(56) References Cited

OTHER PUBLICATIONS

Bijnsdorp et al., Analysis of Drug Interactions. Cancer Cell Culture, Methods and Protocols, Second Edition, Methods in Molecular Biology, vol. 731. Ian A. Cree (Ed.), Humana Press. Chapter 34, pp. 421-434, (2011).

Cavo et al., Prognostic variables and clinical staging in multiple myeloma. Blood. Oct. 1989;74(5):1774-80.

Chavez et al., Triple negative breast cancer cell lines: one tool in the search for better treatment of triple negative breast cancer. Breast Dis. 2010;32(1-2):35-48.

Chou, Drug combination studies and their synergy quantification using the Chou-Talalay method. Cancer Res. Jan. 15, 2010;70(2):440-6.

ClinicalTrials.gov, Bendamustine Hydrochloride in Treating Patients With Recurrent or Progressive Anaplastic Glioma. NIH, U.S. National Library of Medicine. 9 pages, Jul. 7, 2017.

ClinicalTrials.gov, NCT02576496, Study of Tinostamustine, First-in-Class Alkylating HDACi Fusion Molecule, in Relapsed/Refractory Hematologic Malignancies. 12 pages, Sep. 21, 2023.

Davis et al., Platelet effects on ovarian cancer. Semin Oncol. Jun. 2014;41(3):378-84.

Everhard et al., MGMT methylation: a marker of response to temozolomide in low-grade gliomas. Ann Neurol. Dec. 2006;60(6):740-3.

Fan et al., Prognostic Significance of Blood Transfusion in Newly Diagnosed Multiple Myeloma Patients without Autologous Hematopoietic Stem Cell Transplantation. Biomed Res Int. 2017;2017:5462087, 6 pages.

Gemmill et al., Synergistic growth inhibition by Iressa and Rapamycin is modulated by VHL mutations in renal cell carcinoma. Br J Cancer. Jun. 20, 2005;92(12):2266-77.

Guntner et al., Cerebrospinal fluid penetration of targeted therapeutics in pediatric brain tumor patients. Acta Neuropathol Commun. Jun. 3, 2020;8(1):78, 13 pages.

Hartmann et al., Bendamustine hydrochloride in patients with refractory soft tissue sarcoma: a noncomparative multicenter phase 2 study of the German sarcoma group (AIO-001). Cancer. Aug. 15, 2007;110(4):861-6.

Haymarket Media, Inc., Multiple Myeloma Treatment Regimens (Part 1 of 9). Retrieved online at: https://www.cancertherapyadvisor.com/wp-content/uploads/12/2018/12/multiplemyeloma_2017_r_80255.pdf. 9 pages, Oct. 2017.

Koster et al., Carboplatin in Combination with Bendamustine in Previously Untreated Patients with Extensive-Stage Small Cell Lung Cancer (SCLC). Clin Drug Investig. 2004;24(10):611-8.

Lin et al., The antiproliferative effect of C2-ceramide on lung cancer cells through apoptosis by inhibiting Akt and NF?B. Cancer Cell Int. Jan. 6, 2014;14(1):1, 7 pages.

Loibl et al., Multicenter Phase II Study with Weekly Bendamustine and Paclitaxel as First- or Later-Line Therapy in Patients with Metastatic Breast Cancer: RiTa II Trial. Breast Care (Basel). Dec. 2011;6(6):457-461.

Moisan et al., Enhancement of paclitaxel and carboplatin therapies by CCL2 blockade in ovarian cancers. Mol Oncol. Oct. 2014;8(7):1231-9.

Palmer et al., Combination Cancer Therapy Can Confer Benefit via Patient-to-Patient Variability without Drug Additivity or Synergy. Cell. Dec. 14, 2017;171(7):1678-1691.

Rajkumar et al., Multiple Myeloma: Diagnosis and Treatment. Mayo Clin Proc. Jan. 2016;91(1):101-19.

Serra et al., Co-clinical trial of olaparib in breast and ovarian patient-derived tumor xenografts (PDX) enables the identification of response biomarkers. Clin Cancer Res. 2016;22(Suppl 16):Abstract B02, 4 pages.

Siegel et al., Vorinostat in combination with lenalidomide and dexamethasone in patients with relapsed or refractory multiple myeloma. Blood Cancer J. Feb. 21, 2014;4(2):e182, 6 pages.

Tseng et al., A comparison of the molecular subtypes of triple-negative breast cancer among non-Asian and Taiwanese women. Breast Cancer Res Treat. Jun. 2017;163(2):241-254.

White, FDA accepts Mundipharma EDO's IND for EDO-S101. European Pharmaceutical Review. 4 pages, Aug. 3, 2015.

\* cited by examiner

COMPOUNDS FOR TREATING LYMPHOMA OR A T-CELL MALIGNANT DISEASE

REFERENCE TO RELATED APPLICATIONS

This application is a U.S. national stage application filed under 35 U.S.C. § 371, based on International Patent Application No. PCT/IB2019/061034, filed on Dec. 18, 2019, which claims priority to UK Patent Application No. 1820645.8, filed on Dec. 18, 2018, UK Patent Application No. 1820643.3, filed Dec. 18, 2018, UK Patent Application No. 1903003.0, filed Mar. 6, 2019, UK Patent Application No. 1903005.5, filed Mar. 6, 2019, UK Patent Application No. 1908434.2, filed Jun. 12, 2019, and UK Patent Application No. 1908436.7, filed on Jun. 12, 2019, the entire contents of each of the foregoing applications are incorporated herein by reference.

The invention relates to tinostamustine for use in the treatment of lymphoma or a T-cell malignant disease.

BACKGROUND OF THE INVENTION

Lymphoma is a cancer of the lymphatic system. There are two main types of lymphoma, namely Hodgkin lymphoma and non Hodgkin lymphoma.

Non-Hodgkin lymphoma is the more common form of lymphoma. The lymphatic system runs throughout the body, and it is therefore possible to find non-Hodgkin lymphoma in almost all parts of the body. In patients with non-Hodgkin lymphoma, some of their white blood cells (lymphocytes) divide abnormally. They do not have any resting time like normal cells and they start to divide continuously, so too many are produced which do not naturally die. These cells start to divide before they are fully mature and therefore cannot fight infection as normal white blood cells do. The abnormal lymphocytes start to collect in the lymph nodes or other places such as the bone marrow or spleen. They can then grow into tumours and begin to cause problems within the lymphatic system or the organ in which they are growing. For example, if a lymphoma starts in the thyroid gland it can affect the normal production of thyroid hormones. There are many different types of non-Hodgkin lymphoma. They can be classified in several different ways. One way is by the type of cell affected. In non-Hodgkin lymphoma two types of lymphocyte can be affected—B cells and T cells. This is classified as a B cell lymphoma or a T cell lymphoma. Most people with non-Hodgkin lymphoma have B cell lymphomas. T cell lymphomas are more common in teenagers and young adults.

The cells of Hodgkin lymphoma have a particular appearance under the microscope. These cells are called Reed Sternberg cells. Non Hodgkin lymphomas do not have Reed Sternberg cells. It is important for doctors to be able to tell the difference between Hodgkin lymphoma and non-Hodgkin lymphoma cells as they are two different diseases. In Hodgkin lymphoma, it is cells in the lymph nodes that have become cancerous.

The % survival rate over five years in 2009 for patients with non-Hodgkin lymphoma was 63%, while the survival rate for those with Hodgkin lymphoma over the same period was 83%.

T-cell malignant diseases include T-cell prolymphocytic leukemia, which is a rare and unusual malignancy characterized by the proliferation of small- to medium-sized prolymphocytes of postthymic origin with distinctive clinical, morphologic, immunophenotypic, and cytogenetic features. Involvement of the peripheral blood, bone marrow, lymph nodes, liver, spleen, and skin can occur. The clinical course is typically very aggressive with poor response to conventional chemotherapy and short survival rates.

Chemotherapy involves the disruption of cell replication or cell metabolism. However, because of the difficulty in targeting the cancer cells specifically, chemotherapy often causes serious toxic adverse effects. Accordingly, there is a need for more effective cancer treatments, in particular for the treatment of lymphoma. In particular, there is a need for methods of treatment which use the highest possible dose of the chemotherapeutic and therefore provide the maximum therapeutic benefit. However, advantageously, this dose should be tailored, and not exceed the maximum dose that can be tolerated by the particular patient.

WO 2010/085377 discloses tinostamustine (or EDO-S101), which is a first-in-class alkylating deacetylase inhibiting molecule:

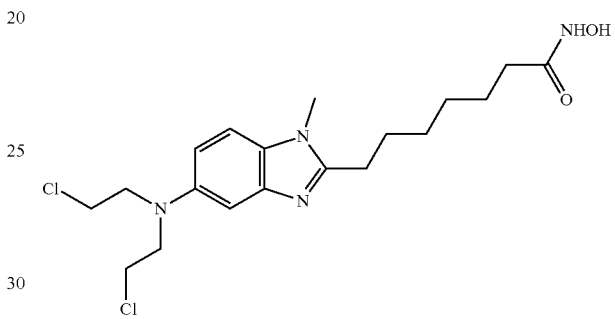

Tinostamustine has shown potent activity in in vitro and in vivo models against lymphoma (see The First-In-Class Alkylating Histone Deacetylase Inhibitor (HDACi) Fusion Molecule EDO-S101 Exerts Potent Preclinical Activity Against Tumor Cells of Hodgkin Lymphoma (HL) Including Bendamustine Resistant Clones, Di Filippi R et al, 57th Annual Meeting and Exposition of the American Society of Hematology (ASH), 6 Dec. 2015.).

SUMMARY OF THE INVENTION

In a first aspect the present invention provides tinostamustine or a pharmaceutically acceptable salt thereof for use in the treatment of lymphoma or a T-cell malignant disease in a patient, wherein the treatment involves:

(a) determining whether the patient's initial platelet count is equal to or above a first value, equal to or below a second value, or between the first and second values, wherein the first value is greater than the second value; and (b) if the initial platelet count is above the first value then administering a first amount of the tinostamustine or pharmaceutically acceptable salt thereof to the patient, if the initial platelet count is equal to or below the second value then administering a second amount of the tinostamustine, and if the initial platelet count is between the first and second values then administering a third amount of the tinostamustine, wherein the first amount is greater than the third amount and the third amount is greater than the second amount.

In a first aspect the present invention also provides a use of tinostamustine or a pharmaceutically acceptable salt thereof for the manufacture of a medicament for use in the treatment of lymphoma or a T-cell malignant disease in a patient, wherein the treatment involves:

(a) determining whether the patient's initial platelet count is above or below a particular value; and (b) if the initial platelet count is above the particular value then administering a first amount of the tinostamustine or pharmaceutically acceptable salt thereof to the patient, and if the initial platelet count is below the particular value then administering a second amount of the tinostamustine or pharmaceutically acceptable salt thereof to the patient, wherein the first amount is greater than the second amount.

In a first aspect the present invention also provides a method of treating lymphoma or a T-cell malignant disease in a patient comprising the steps of:

(a) determining whether the patient's initial platelet count is above or below a particular value; and (b) if the initial platelet count is above the particular value then administering a first amount of tinostamustine or a pharmaceutically acceptable salt thereof to the patient, and if the initial platelet count is below the particular value then administering a second amount of tinostamustine or pharmaceutically acceptable salt thereof to the patient, wherein the first amount is greater than the second amount.

In a second aspect, the present invention provides tinostamustine or a pharmaceutically acceptable salt thereof for use in the treatment of lymphoma or a T-cell malignant disease in a patient, wherein the patient has a baseline platelet count of greater than or equal to $200 \times 10^9$/L and the tinostamustine or pharmaceutically acceptable salt thereof is administered at a dose of 95 mg/m$^2$ or greater (for example 95-105 mg/m$^2$ e.g. 100 mg/m$^2$) based on free tinostamustine and the patient's body surface area.

In a second aspect, the present invention also provides a use of tinostamustine or a pharmaceutically acceptable salt thereof for the manufacture of a medicament for use in the treatment of lymphoma or a T-cell malignant disease in a patient, wherein the patient has a baseline platelet count of greater than or equal to $200 \times 10^9$/L and the tinostamustine or pharmaceutically acceptable salt thereof is administered at a dose of 95 mg/m$^2$ or greater (for example 95-105 mg/m$^2$ e.g. 100 mg/m$^2$) based on free tinostamustine and the patient's body surface area.

In a second aspect, the present invention also provides a method of treating lymphoma or a T-cell malignant disease in a patient wherein the patient has a baseline platelet count of greater than or equal to $200 \times 10^9$/L, comprising the step of administering to the patient tinostamustine or a pharmaceutically acceptable salt thereof at a dose of 95 mg/m$^2$ or greater (for example 95-105 mg/m$^2$ e.g. 100 mg/m$^2$) based on free tinostamustine and the patient's body surface area.

In a third aspect, the present invention provides tinostamustine or a pharmaceutically acceptable salt thereof for use in the treatment of lymphoma or a T-cell malignant disease in a patient, wherein the patient has a baseline platelet count of between $100 \times 10^9$/L and $200 \times 10^9$/L and the tinostamustine or pharmaceutically acceptable salt thereof is administered at a dose of 75-85 mg/m$^2$ (for example 80 mg/m$^2$) based on free tinostamustine and the patient's body surface area.

In a third aspect, the present invention also provides the use of tinostamustine or a pharmaceutically acceptable salt thereof for the manufacture of a medicament for use in the treatment of lymphoma or a T-cell malignant disease in a patient, wherein the patient has a baseline platelet count of between $100 \times 10^9$/L and $200 \times 10^9$/L and the tinostamustine or pharmaceutically acceptable salt thereof is administered at a dose of 75-85 mg/m$^2$ (for example 80 mg/m$^2$) based on free tinostamustine and the patient's body surface area.

In a third aspect, the present invention provides a method of treating lymphoma or a T-cell malignant disease in a patient wherein the patient has a baseline platelet count of between $100 \times 10^9$/L and $200 \times 10^9$/L, comprising the step of administering to the patient tinostamustine or a pharmaceutically acceptable salt thereof at a dose of 75-85 mg/m$^2$ (for example 80 mg/m$^2$) based on free tinostamustine and the patient's body surface area.

In a fourth aspect, the present invention provides tinostamustine or a pharmaceutically acceptable salt thereof for use in the treatment of lymphoma or a T-cell malignant disease in a patient, wherein the patient has a baseline platelet count of less than or equal to $100 \times 10^9$/L and the tinostamustine or pharmaceutically acceptable salt thereof is administered at a dose of 54 mg/m$^2$ or lower (for example 45-54 mg/m$^2$ e.g. 50 mg/m$^2$) based on free tinostamustine and the patient's body surface area.

In a fourth aspect, the present invention also provides a use of tinostamustine or a pharmaceutically acceptable salt thereof for the manufacture of a medicament for use in the treatment of lymphoma or a T-cell malignant disease in a patient, wherein the patient has a baseline platelet count of less than or equal to $100 \times 10^9$/L and the tinostamustine or pharmaceutically acceptable salt thereof is administered at a dose of 54 mg/m$^2$ or lower (for example 45-54 mg/m$^2$ e.g. 50 mg/m$^2$) based on free tinostamustine and the patient's body surface area.

In a fourth aspect, the present invention also provides a method of treating lymphoma or a T-cell malignant disease in a patient wherein the patient has a baseline platelet count of less than or equal to $100 \times 10^9$/L, comprising the step of administering to the patient tinostamustine or a pharmaceutically acceptable salt thereof at a dose 54 mg/m$^2$ or lower (for example 45-54 mg/m$^2$ e.g. 50 mg/m$^2$) based on free tinostamustine and the patient's body surface area.

In a fifth aspect, the present invention provides tinostamustine or a pharmaceutically acceptable salt thereof for use in the treatment of lymphoma or a T-cell malignant disease in a patient, wherein the tinostamustine or pharmaceutically acceptable salt thereof is administered:

intravenously;

at a dose of from 20-100 mg/m$^2$ based on free tinostamustine and the patient's body surface area, for example 95-105 mg/m$^2$, 75-85 mg/m$^2$, 55-65 mg/m$^2$, 45-55 mg/m$^2$ or 35-45 mg/m$^2$ (e.g. 100 mg/m$^2$; 80 mg/m$^2$, 60 mg/m$^2$, 50 mg/m$^2$ or 40 mg/m$^2$); and over a period of time which is 45-75 minutes, for example 50-70 minutes or 55-65 minutes e.g. 60 minutes.

In a fifth aspect, the present invention provides tinostamustine or a pharmaceutically acceptable salt thereof for the manufacture of a medicament for use in the treatment of lymphoma or a T-cell malignant disease in a patient, wherein the tinostamustine or pharmaceutically acceptable salt thereof is administered:

intravenously;

at a dose of from 20-100 mg/m$^2$ based on free tinostamustine and the patient's body surface area, for example 95-105 mg/m$^2$, 75-85 mg/m$^2$, 55-65 mg/m$^2$, 45-55 mg/m$^2$ or 35-45 mg/m$^2$ (e.g. 100 mg/m$^2$; 80 mg/m$^2$, 60 mg/m$^2$, 50 mg/m$^2$ or 40 mg/m$^2$); and over a period of time which is 45-75 minutes, for example 50-70 minutes or 55-65 minutes e.g. 60 minutes.

In a fifth aspect, the present invention also provides a method of treating lymphoma or a T-cell malignant disease in a patient comprising the step of administering to the patient tinostamustine or a pharmaceutically acceptable salt thereof:

intravenously;
at a dose of from 20-100 mg/m² based on free tinostamustine and the patient's body surface area, for example 95-105 mg/m², 75-85 mg/m², 55-65 mg/m², 45-55 mg/m² or 35-45 mg/m² (e.g. 100 mg/m²; 80 mg/m², 60 mg/m², 50 mg/m² or 40 mg/m²); and
over a period of time which is 45-75 minutes, for example 50-70 minutes or 55-65 minutes e.g. 60 minutes.

BRIEF DESCRIPTION OF THE FIGURES

The invention will be described with reference to the following figures, wherein.

DEFINITIONS

Dose of Tinostamustine

Figure 1:
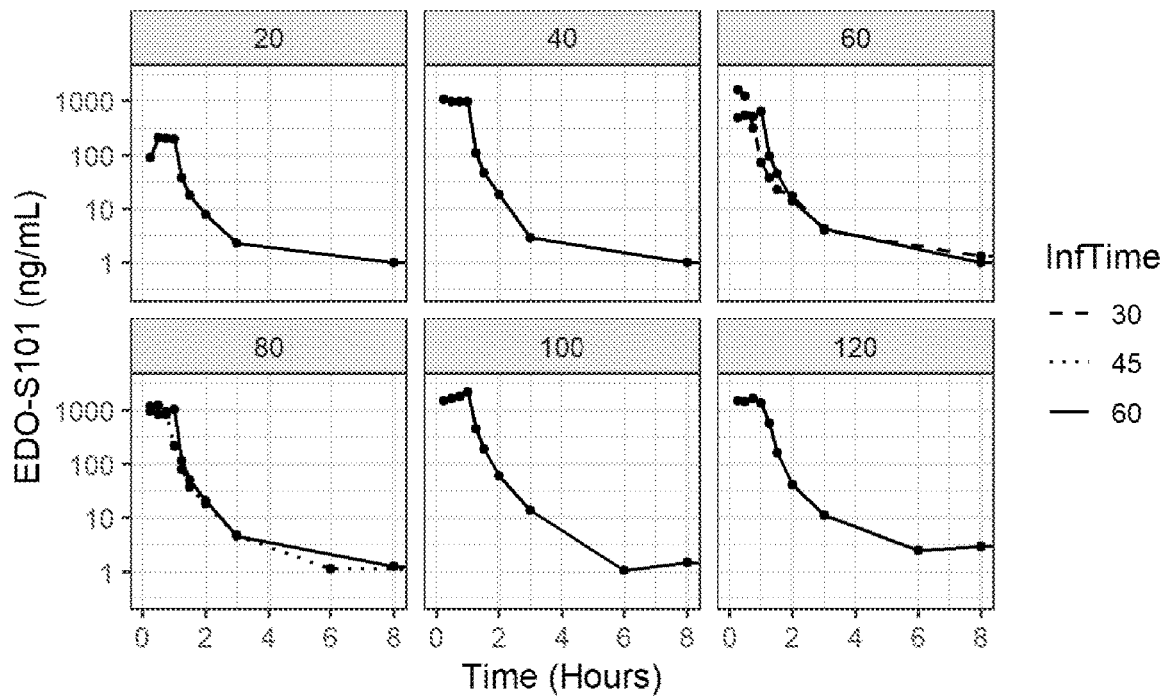
FIG. 1 shows the day one median PK profiles of tinostamustine by dose group.

The dose of tinostamustine is defined herein by reference to free tinostamustine. The term free tinostamustine means tinostamustine that is not in the form of a pharmaceutically acceptable salt. In the event that the invention is implemented using a salt of tinostamustine, then the mass of the salt administered is adjusted to provide the same number of moles of tinostamustine as is present in the masses of free tinostamustine defined herein.

Patient Surface Area

The dose of tinostamustine is defined herein by reference to amount of free tinostamustine used relative to the patient's surface area i.e. mg/m². The skilled clinician is able to calculate the patient surface area using the common general knowledge.

In particular, patient surface area (PSA) can be calculated using the following formula (Dubois D, Dubois EF, A formula to estimate the approximate surface area if height and weight be known, Arch Intern Med, 1916, 17, 863-871):

$$PSA = 0.007184 \times (\text{patient height in cm})^{0.725} \times (\text{patient weight in kg})^{0.425}$$

Platelet Count

Platelets, also known as thrombocytes, are a component of blood that reacts to bleeding by clumping and thereby initiating a blood clot. The platelet count of a patient can be determined by part of a routine complete blood count in which a sample of blood is taken and then analysed to give the number of platelets per litre of blood.

The platelet count can be measured in two ways, namely a manual visual method and an automated electronic method.

A visual platelet count may be determined manually using a hemocytometer, where the number of platelets can be counted in a specific volume of blood.

An electronic method uses an automated blood cell analyser (e.g. a Coulter S-Plus) which counts particles in the bloodstream. However, for very low counts e.g. below $50 \times 10^9$/L, an electronic measurement may not be accurate and should be confirmed by a manual count.

A low platelet concentration (less than $150 \times 10^9$/L) is known as thrombocytopenia and can be a result of decreased production or depletion.

Claim Format

In the general aspects of invention described above, the invention is described using the European compound-for-use medical use format, the Swiss-format and method of treatment format. For the sake of conciseness, in the following detailed description we have defined the invention using only the compound-for-use format. However, these passages should also be considered to further define the invention in the method of treatment format and Swiss-format.

The invention is defined herein by reference to the treatment of the disease. The term treatment should be interpreted to cover prophylaxis too, by which is meant in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

DETAILED DESCRIPTION OF THE INVENTION

The present invention relates to tinostamustine or a pharmaceutically acceptable salt thereof for use in the treatment of lymphoma or a T-cell malignant disease.

As discussed, it is desirable to calculate the maximum dose that can be tolerated by a particular patient. This allows each patient to obtain the maximum possible therapeutic benefit while minimising the risk of unacceptable and possibly fatal adverse chemotherapeutic effects. Prior to performing the phase 1 human trial, the skilled person would not have predicted what adverse effects would limit the maximum tolerated dose. Early studies suggested that the dose may be limited by cardiac safety.

However, surprisingly, the applicant found that thrombocytopenia was dose limiting. Further, the applicant discovered that the probability of developing thrombocytopenia could be predicted solely by the patient's baseline platelet count. Accordingly, the invention provides an improved treatment, wherein the maximum dose that can be tolerated by a particular patient can be calculated by measuring their platelet count prior to therapy, in order to provide the best possible balance between therapeutic and adverse effects.

Accordingly, in a first aspect the present invention provides tinostamustine or a pharmaceutically acceptable salt thereof for use in the treatment of lymphoma or a T-cell malignant disease in a patient, wherein the treatment involves:

(a) determining whether the patient's initial platelet count is equal to or above a first value, equal to or below a second value, or between the first and second values, wherein the first value is greater than the second value; and (b) if the initial platelet count is above the first value then administering a first amount of the tinostamustine or pharmaceutically acceptable salt thereof to the patient, if the initial platelet count is equal to or below the second value then administering a second amount of the tinostamustine, and if the initial platelet count is between the first and second values then administering a third amount of the tinostamustine, wherein the first amount is greater than the third amount and the third amount is greater than the second amount.

In particular, the patient is a human.

Thus, prior to administration, the patient to be treated has their platelet count measured, and based on the platelet count the appropriate amount of tinostamustine to be administered is determined. In particular, if a patient has a higher platelet count, then the patient can tolerate a higher dose of tinostamustine. If a patient has a lower platelet count, a lower dose of tinostamustine can be tolerated.

In particular embodiments, the patient's initial platelet count is determined to be equal to or above a first value which is:
between $165\times10^9$/L and $175\times10^9$/L;
between $170\times10^9$/L and $180\times10^9$/L;
between $175\times10^9$/L and $185\times10^9$/L;
between $180\times10^9$/L and $190\times10^9$/L;
between $190\times10^9$/L and $200\times10^9$/L;
between $195\times10^9$/L and $205\times10^9$/L;
between $200\times10^9$/L and $210\times10^9$/L;
between $205\times10^9$/L and $215\times10^9$/L;
between $210\times10^9$/L and $220\times10^9$/L; and
between $215\times10^9$/L and $225\times10^9$/L.

Preferably, the patient's initial platelet count is determined to be equal to or above a first value which is $200\times10^9$/L.

In other embodiments, the patient's initial platelet count is determined to be equal to or above a first value which is:
$170\times10^9$/L;
$175\times10^9$/L;
$180\times10^9$/L;
$185\times10^9$/L;
$190\times10^9$/L;
$195\times10^9$/L;
$205\times10^9$/L;
$210\times10^9$/L;
$215\times10^9$/L; or
$220\times10^9$/L.

Preferably, if the patient's platelet count is determined to be equal to or above the first value, then the amount of tinostamustine or pharmaceutically acceptable salt thereof is 95 mg/m² or greater (for example 95-105 mg/m² e.g. 100 mg/m²) based on free tinostamustine and the patient's body surface area. In particular, if the patient's platelet count is determined to be over the relevant value, then the amount of tinostamustine or pharmaceutically acceptable salt thereof is 100 mg/m² based on free tinostamustine and the patient's body surface area.

In other embodiments, if the patient's platelet count is determined to be over the relevant value, then the amount of tinostamustine or pharmaceutically acceptable salt thereof is:
from 75 to 85 mg/m² (e.g. 80 mg/m²) based on free tinostamustine and the patient's body surface area;
from 80 to 90 mg/m² (e.g. 85 mg/m²) based on free tinostamustine and the patient's body surface area;
from 85 to 105 mg/m² (e.g. 90 mg/m²) based on free tinostamustine and the patient's body surface area;
from 90 to 100 mg/m² (e.g. 95 mg/m²) based on free tinostamustine and the patient's body surface area;
from 100 to 110 mg/m² (e.g. 105 mg/m²) based on free tinostamustine and the patient's body surface area;
from 105 to 115 mg/m² (e.g. 110 mg/m²) based on free tinostamustine and the patient's body surface area;
from 110 to 120 mg/m² (e.g. 115 mg/m²) based on free tinostamustine and the patient's body surface area; or
from 115 to 125 mg/m² (e.g. 120 mg/m²) based on free tinostamustine and the patient's body surface area.

In particular embodiments, the patient's initial platelet count is determined to be equal to or below a second value which is:
between $65\times10^9$/L and $75\times10^9$/L;
between $70\times10^9$/L and $80\times10^9$/L;
between $75\times10^9$/L and $85\times10^9$/L;
between $80\times10^9$/L and $90\times10^9$/L;
between $90\times10^9$/L and $100\times10^9$/L;
between $95\times10^9$/L and $105\times10^9$/L;
between $100\times10^9$/L and $110\times10^9$/L;
between $105\times10^9$/L and $115\times10^9$/L;
between $110\times10^9$/L and $120\times10^9$/L; and
between $115\times10^9$/L and $125\times10^9$/L.

Preferably, the patient's initial platelet count is determined to be equal to or below a second value which is $100\times10^9$/L.

In other embodiments, the patient's initial platelet count is determined to be equal to or below a second value which is:
$70\times10^9$/L;
$75\times10^9$/L;
$80\times10^9$/L;
$85\times10^9$/L;
$90\times10^9$/L;
$95\times10^9$/L;
$105\times10^9$/L;
$110\times10^9$/L;
$115\times10^9$/L; or $-120\times10^9$/L.

Preferably, if the patient's platelet count is determined to be equal to or below the second value, then the amount of tinostamustine or pharmaceutically acceptable salt thereof is 54 mg/m² or lower (for example 45-54 mg/m² e.g. 50 mg/m²) based on free tinostamustine and the patient's body surface area. In particular, if the patient's platelet count is determined to be over the relevant value, then the amount of tinostamustine or pharmaceutically acceptable salt thereof is 50 mg/m² based on free tinostamustine and the patient's body surface area.

In other embodiments, if the patient's platelet count is determined to be equal to or below the second value, then the amount of tinostamustine or pharmaceutically acceptable salt thereof is:
from 25 to 35 mg/m² (e.g. 30 mg/m²) based on free tinostamustine and the patient's body surface area;
from 30 to 40 mg/m² (e.g. 35 mg/m²) based on free tinostamustine and the patient's body surface area;
from 35 to 45 mg/m² (e.g. 40 mg/m²) based on free tinostamustine and the patient's body surface area;
from 40 to 50 mg/m² (e.g. 45 mg/m²) based on free tinostamustine and the patient's body surface area;
from 50 to 60 mg/m² (e.g. 55 mg/m²) based on free tinostamustine and the patient's body surface area;
from 55 to 65 mg/m² (e.g. 60 mg/m²) based on free tinostamustine and the patient's body surface area;
from 60 to 70 mg/m² (e.g. 65 mg/m²) based on free tinostamustine and the patient's body surface area; or
from 65 to 75 mg/m² (e.g. 70 mg/m²) based on free tinostamustine and the patient's body surface area.

In particular embodiments, the patient's initial platelet count is determined to be within a range defined by first and second values which is:

75-175×10$^9$/L;
80-180×10$^9$/L;
85-185×10$^9$/L;
90-100×10$^9$/L;
95-195×10$^9$/L;
105-205×10$^9$/L;
110-210×10$^9$/L;
115-215×10$^9$/L; or
120-220×10$^9$/L.

Preferably, the patient's initial platelet count is determined to be within a range defined by first and second values which is 100-200×10$^9$/L.

Preferably, if the patient's platelet count is determined to be within a range defined by first and second values, then the amount of tinostamustine or pharmaceutically acceptable salt thereof is 75-85 mg/m$^2$ (for example 80 mg/m$^2$) based on free tinostamustine and the patient's body surface area. In particular, if the patient's platelet count is determined to be within a range defined by first and second values, then the amount of tinostamustine or pharmaceutically acceptable salt thereof is 80 mg/m$^2$ based on free tinostamustine and the patient's body surface area.

In other embodiments, if the patient's platelet count is determined to be within a range defined by first and second values, then the amount of tinostamustine or pharmaceutically acceptable salt thereof is:
from 55 to 65 mg/m$^2$ (e.g. 60 mg/m$^2$) based on free tinostamustine and the patient's body surface area;
from 60 to 70 mg/m$^2$ (e.g. 65 mg/m$^2$) based on free tinostamustine and the patient's body surface area;
from 65 to 75 mg/m$^2$ (e.g. 70 mg/m$^2$) based on free tinostamustine and the patient's body surface area;
from 70 to 80 mg/m$^2$ (e.g. 75 mg/m$^2$) based on free tinostamustine and the patient's body surface area;
from 80 to 90 mg/m$^2$ (e.g. 85 mg/m$^2$) based on free tinostamustine and the patient's body surface area;
from 85 to 95 mg/m$^2$ (e.g. 90 mg/m$^2$) based on free tinostamustine and the patient's body surface area;
from 90 to 100 mg/m$^2$ (e.g. 95 mg/m$^2$) based on free tinostamustine and the patient's body surface area; or
from 95 to 105 mg/m$^2$ (e.g. 100 mg/m$^2$) based on free tinostamustine and the patient's body surface area.

Accordingly, the invention provides tinostamustine or a pharmaceutically acceptable salt thereof for use in the treatment of lymphoma or a T-cell malignant disease in a patient wherein:
(i) if the patient's initial platelet count is greater than or equal to 200×10$^9$/L then the amount of tinostamustine or pharmaceutically acceptable salt thereof is 95 mg/m$^2$ or greater (for example 95-105 mg/m$^2$ e.g. 100 mg/m$^2$) based on free tinostamustine and the patient's body surface area; and
(ii) if the patient's initial platelet count is less than or equal to 100×10$^9$/L then the amount of tinostamustine or pharmaceutically acceptable salt thereof is 54 mg/m$^2$ or lower (for example 45-54 mg/m$^2$ e.g. 50 mg/m$^2$) based on free tinostamustine and the patient's body surface area; and
(iii) if the patient's initial platelet count is between 100×10$^9$/L and 200×10$^9$/L then the amount of tinostamustine or pharmaceutically acceptable salt thereof is 75-85 mg/m$^2$ (for example 80 mg/m$^2$) based on free tinostamustine and the patient's body surface area.

In particular, the invention provides tinostamustine or a pharmaceutically acceptable salt thereof for use in the treatment of lymphoma or a T-cell malignant disease in a patient wherein:
(i) if the patient's initial platelet count is greater than or equal to 200×10$^9$/L then the amount of tinostamustine or pharmaceutically acceptable salt thereof is 100 mg/m$^2$ based on free tinostamustine and the patient's body surface area; and
(ii) if the patient's initial platelet count is less than or equal to 100×10$^9$/L then the amount of tinostamustine or pharmaceutically acceptable salt thereof is 50 mg/m$^2$ based on free tinostamustine and the patient's body surface area; and
(iii) if the patient's initial platelet count is between 100×10$^9$/L and 200×10$^9$/L then the amount of tinostamustine or pharmaceutically acceptable salt thereof is 80 mg/m$^2$ based on free tinostamustine and the patient's body surface area.

In a second aspect, the present invention provides tinostamustine or a pharmaceutically acceptable salt thereof for use in the treatment of lymphoma or a T-cell malignant disease in a patient, wherein the patient has a baseline platelet count of greater than or equal to 200×10$^9$/L and the tinostamustine or pharmaceutically acceptable salt thereof is administered at a dose of 95 mg/m$^2$ or greater (for example 95-105 mg/m$^2$ e.g. 100 mg/m$^2$) based on free tinostamustine and the patient's body surface area.

In particular, the invention provides tinostamustine or a pharmaceutically acceptable salt thereof for use in the treatment of lymphoma or a T-cell malignant disease in a patient, wherein the patient has a baseline platelet count of greater than or equal to 200×10$^9$/L and the tinostamustine or pharmaceutically acceptable salt thereof is administered at a dose of 100 mg/m$^2$ based on free tinostamustine and the patient's body surface area.

In other particular embodiments, the invention provides tinostamustine or a pharmaceutically acceptable salt thereof for use in the treatment of lymphoma or a T-cell malignant disease in a patient, wherein the patient has a baseline platelet count equal to or above a first value which is:
170×10$^9$/L;
175×10$^9$/L;
180×10$^9$/L;
185×10$^9$/L;
190×10$^9$/L;
195×10$^9$/L;
205×10$^9$/L;
210×10$^9$/L;
215×10$^9$/L; or
220×10$^9$/L;
and the tinostamustine or pharmaceutically acceptable salt thereof is administered at a dose of 95 mg/m$^2$ or greater (for example 95-105 mg/m$^2$ e.g. 100 mg/m$^2$) based on free tinostamustine and the patient's body surface area.

In other particular embodiments, the invention provides tinostamustine or a pharmaceutically acceptable salt thereof for use in the treatment of lymphoma or a T-cell malignant disease in a patient, wherein the patient has a baseline platelet count of equal to or greater than 200×10$^9$/L and the tinostamustine or pharmaceutically acceptable salt thereof is administered at a dose of:
80 mg/m$^2$ based on free tinostamustine and the patient's body surface area;
85 mg/m$^2$ based on free tinostamustine and the patient's body surface area;
90 mg/m$^2$ based on free tinostamustine and the patient's body surface area;
95 mg/m$^2$ based on free tinostamustine and the patient's body surface area;

105 mg/m² based on free tinostamustine and the patient's body surface area;
110 mg/m² based on free tinostamustine and the patient's body surface area;
115 mg/m² based on free tinostamustine and the patient's body surface area;
120 mg/m² based on free tinostamustine and the patient's body surface area.

Other possible combinations of platelet levels and doses are as follows:

| | | Dose based on free tinostamustine (mg/m²) | | | | | | | |
|---|---|---|---|---|---|---|---|---|---|
| | | 75-85 | 80-90 | 85-95 | 90-100 | 95-105 | 100-110 | 105-115 | 110-120 |
| Platelet level greater than or equal to (×10⁹/L) | 170 | A1 | B1 | C1 | D1 | E1 | F1 | G1 | H1 |
| | 175 | A2 | B2 | C2 | D2 | E2 | F2 | G2 | H2 |
| | 180 | A3 | B3 | C3 | D3 | E3 | F3 | G3 | H3 |
| | 185 | A4 | B4 | C4 | D4 | E4 | F4 | G4 | H4 |
| | 190 | A5 | B5 | C5 | D5 | E5 | F5 | G5 | H5 |
| | 195 | A6 | B6 | C6 | D6 | E6 | F6 | G6 | H6 |
| | 200 | A7 | B7 | C7 | D7 | E7 | F7 | G7 | H7 |
| | 205 | A8 | B8 | C8 | D8 | E8 | F8 | G8 | H8 |
| | 210 | A9 | B9 | C9 | D9 | E9 | F9 | G9 | H9 |
| | 215 | A10 | B10 | C10 | D10 | E10 | F10 | G10 | H10 |
| | 220 | A11 | B11 | C11 | D11 | E11 | F11 | G11 | H11 |

In other particular embodiments, the invention provides tinostamustine or a pharmaceutically acceptable salt thereof for use in the treatment of lymphoma or a T-cell malignant disease in a patient, wherein the patient baseline platelet count and the dose of tinostamustine or pharmaceutically acceptable salt thereof is selected from anyone of A1-A11, B1-B11, C1-C11, D1-D11, E1-E11, F1-F11, G1-G11 or H1-H11 as defined in the table above.

In a third aspect, the present invention provides tinostamustine or a pharmaceutically acceptable salt thereof for use in the treatment of lymphoma or a T-cell malignant disease in a patient, wherein the patient has a baseline platelet count of between 100×10⁹/L and 200×10⁹/L and the tinostamustine or pharmaceutically acceptable salt thereof is administered at a dose of 75-85 mg/m² (for example 80 mg/m²) based on free tinostamustine and the patient's body surface area.

In particular, the invention provides tinostamustine or a pharmaceutically acceptable salt thereof for use in the treatment of lymphoma or a T-cell malignant disease in a patient, wherein the patient has a baseline platelet count of between 100×10⁹/L and 200×10⁹/L and the tinostamustine or pharmaceutically acceptable salt thereof is administered at a dose of 80 mg/m² based on free tinostamustine and the patient's body surface area.

In other particular embodiments, the invention provides tinostamustine or a pharmaceutically acceptable salt thereof for use in the treatment of lymphoma or a T-cell malignant disease in a patient, wherein the patient has a baseline platelet count which is:
75-175×10⁹/L;
80-180×10⁹/L;
85-185×10⁹/L;
90-100×10⁹/L;
95-195×10⁹/L;
105-205×10⁹/L;
110-210×10⁹/L;
115-215×10⁹/L; or
120-220×10⁹/L;
and the tinostamustine or pharmaceutically acceptable salt thereof is administered at a dose of 75-85 mg/m² (for example 80 mg/m²) based on free tinostamustine and the patient's body surface area.

In other particular embodiments, the invention provides tinostamustine or a pharmaceutically acceptable salt thereof for use in the treatment of lymphoma or a T-cell malignant disease in a patient, wherein the patient has a baseline platelet count of between 100×10⁹/L and 200×10⁹/L and the tinostamustine or pharmaceutically acceptable salt thereof is administered at a dose of:
60 mg/m² based on free tinostamustine and the patient's body surface area;
65 mg/m² based on free tinostamustine and the patient's body surface area;
70 mg/m² based on free tinostamustine and the patient's body surface area;
75 mg/m² based on free tinostamustine and the patient's body surface area;
85 mg/m² based on free tinostamustine and the patient's body surface area;
90 mg/m² based on free tinostamustine and the patient's body surface area;
95 mg/m² based on free tinostamustine and the patient's body surface area; or
700 mg/m² based on free tinostamustine and the patient's body surface area.

Other possible combinations of platelet levels and doses are as follows:

| | | Dose based on free tinostamustine (mg/m²) | | | | | | | |
|---|---|---|---|---|---|---|---|---|---|
| | | 30-40 | 35-45 | 40-50 | 45-55 | 50-60 | 55-65 | 60-70 | 65-75 |
| Platelet level between (×10⁹/L) | 75-175 | A1 | B1 | C1 | D1 | E1 | F1 | G1 | H1 |
| | 80-180 | A2 | B2 | C2 | D2 | E2 | F2 | G2 | H2 |
| | 85-185 | A3 | B3 | C3 | D3 | E3 | F3 | G3 | H3 |
| | 90-190 | A4 | B4 | C4 | D4 | E4 | F4 | G4 | H4 |
| | 95-195 | A5 | B5 | C5 | D5 | E5 | F5 | G5 | H5 |
| | 100-200 | A6 | B6 | C6 | D6 | E6 | F6 | G6 | H6 |
| | 105-205 | A7 | B7 | C7 | D7 | E7 | F7 | G7 | H7 |
| | 110-210 | A8 | B8 | C8 | D8 | E8 | F8 | G8 | H8 |
| | 115-215 | A9 | B9 | C9 | D9 | E9 | F9 | G9 | H9 |
| | 120-220 | A10 | B10 | C10 | D10 | E10 | F10 | G10 | H10 |

In other particular embodiments, the invention provides tinostamustine or a pharmaceutically acceptable salt thereof for use in the treatment of lymphoma or a T-cell malignant disease in a patient, wherein the patient baseline platelet count and the dose of tinostamustine or pharmaceutically acceptable salt thereof is selected from anyone of A1-A10, B1-610, C1-C10, D1-D10, E1-E10, F1-F10, G1-G10 or H1-H10 as defined in the table above.

In a fourth aspect, the present invention provides tinostamustine or a pharmaceutically acceptable salt thereof for use in the treatment of lymphoma or a T-cell malignant disease in a patient, wherein the patient has a baseline platelet count of less than or equal to 100×10$^9$/L and the tinostamustine or pharmaceutically acceptable salt thereof is administered at a dose of 54 mg/m$^2$ or lower (for example 45-54 mg/m$^2$ e.g. 50 mg/m$^2$) based on free tinostamustine and the patient's body surface area.

In particular, the present invention provides tinostamustine or a pharmaceutically acceptable salt thereof for use in the treatment of lymphoma or a T-cell malignant disease in a patient, wherein the patient has a baseline platelet count of less than or equal to 100×10$^9$/L and the tinostamustine or pharmaceutically acceptable salt thereof is administered at a dose of 50 mg/m$^2$ based on free tinostamustine and the patient's body surface area.

In other particular embodiments, the invention provides tinostamustine or a pharmaceutically acceptable salt thereof for use in the treatment of lymphoma or a T-cell malignant disease in a patient, wherein the patient has a baseline platelet count of less than or equal to a second value which is:

70×10$^9$/L;

75×10$^9$/L;

80×10$^9$/L;

85×10$^9$/L;

90×10$^9$/L;

95×10$^9$/L;

105×10$^9$/L;

110×10$^9$/L;

115×10$^9$/L; or

120×10$^9$/L;

and the tinostamustine or pharmaceutically acceptable salt thereof is administered at a dose of 54 mg/m$^2$ or lower (for example 45-54 mg/m$^2$ e.g. 50 mg/m$^2$) based on free tinostamustine and the patient's body surface area.

In other particular embodiments, the invention provides tinostamustine or a pharmaceutically acceptable salt thereof for use in the treatment of lymphoma or a T-cell malignant disease in a patient, wherein the patient has a baseline platelet count of less than or equal to a second value which is 100×10$^9$/L and the tinostamustine or pharmaceutically acceptable salt thereof is administered at a dose of:

30 mg/m$^2$ based on free tinostamustine and the patient's body surface area;

35 mg/m$^2$ based on free tinostamustine and the patient's body surface area;

40 mg/m$^2$ based on free tinostamustine and the patient's body surface area;

45 mg/m$^2$ based on free tinostamustine and the patient's body surface area;

55 mg/m$^2$ based on free tinostamustine and the patient's body surface area;

60 mg/m$^2$ based on free tinostamustine and the patient's body surface area;

65 mg/m$^2$ based on free tinostamustine and the patient's body surface area; or 70 mg/m$^2$ based on free tinostamustine and the patient's body surface area.

Other possible combinations of platelet levels and doses are as follows:

| | | Dose based on free tinostamustine (mg/m$^2$) | | | | | | |
|---|---|---|---|---|---|---|---|---|
| | | 30-40 | 35-45 | 40-50 | 45-55 | 50-60 | 55-65 | 60-70 | 65-75 |
| Platelet level equal to or less than (×10$^9$/L) | 70 | A1 | B1 | C1 | D1 | E1 | F1 | G1 | H1 |
| | 75 | A2 | B2 | C2 | D2 | E2 | F2 | G2 | H2 |
| | 80 | A3 | B3 | C3 | D3 | E3 | F3 | G3 | H3 |
| | 85 | A4 | B4 | C4 | D4 | E4 | F4 | G4 | H4 |
| | 90 | A5 | B5 | C5 | D5 | E5 | F5 | G5 | H5 |
| | 95 | A6 | B6 | C6 | D6 | E6 | F6 | G6 | H6 |
| | 100 | A7 | B7 | C7 | D7 | E7 | F7 | G7 | H7 |
| | 105 | A8 | B8 | C8 | D8 | E8 | F8 | G8 | H8 |
| | 110 | A9 | B9 | C9 | D9 | E9 | F9 | G9 | H9 |
| | 115 | A10 | B10 | C10 | D10 | E10 | F10 | G10 | H10 |
| | 120 | A11 | B11 | C11 | D11 | E11 | F11 | G11 | H11 |

In other particular embodiments, the invention provides tinostamustine or a pharmaceutically acceptable salt thereof for use in the treatment of lymphoma or a T-cell malignant disease in a patient, wherein the patient baseline platelet count and the dose of tinostamustine or pharmaceutically acceptable salt thereof is selected from anyone of A1-A11, B1-B11, C1-C11, D1-D11, E1-E11, F1-F11, G1-G11 or H1-H11 as defined in the table above.

In general, the tinostamustine or a pharmaceutically acceptable salt thereof is administered over multiple treatment cycles e.g. 4 to 8 treatment cycles.

In other words, the tinostamustine or a pharmaceutically acceptable salt thereof is administered to the patient and then the patient has a rest period in which no treatment is administered. Each period in which tinostamustine or a pharmaceutically acceptable salt thereof is administered is a treatment cycle.

In one embodiment, the treatment cycle is 21 days i.e. three weeks. In particular, tinostamustine or a pharmaceutically acceptable salt thereof is administered on day 1 of a 21-day treatment cycle.

As mentioned, the invention is based on the surprising finding that the maximum tolerated dose of tinostamustine can be determined by measuring the patient's platelet count before administration. In the embodiment in which the tinostamustine or a pharmaceutically acceptable salt thereof is administered over multiple treatment cycles, the platelet count can be measured before each treatment cycle, to determine the appropriate dose for that cycle.

Accordingly, in one embodiment, the invention provides tinostamustine or a pharmaceutically acceptable salt thereof for use in the treatment of lymphoma or a T-cell malignant disease in a patient, wherein the tinostamustine or a pharmaceutically acceptable salt thereof is administered over multiple treatment cycles and the treatment involves:

(a) determining the patient's platelet count before each subsequent treatment cycle; and (b) (i) if the patient's initial platelet count was greater than or equal to 200×10$^9$/L and the patient's platelet count before the subsequent treatment cycle is greater than or equal to 50×10$^9$/L, then the amount of tinostamustine or pharmaceutically acceptable salt thereof administered in the subsequent treatment cycle is 95 mg/m$^2$ or greater (for example 95-105 mg/m$^2$ e.g. 100 mg/m$^2$) based on free tinostamustine and the patient's body surface area; and (ii) if the patient's initial platelet count was greater than or equal to 200×10$^9$/L and the patient's platelet count before the subsequent treatment cycle is less than 50×10$^9$/L, then the amount of tinostamustine or pharmaceutically acceptable salt thereof administered in the subsequent treatment cycle is 84 mg/m² or lower (for example 75-84 mg/m² e.g. 80 mg/m²) based on free tinostamustine and the patient's body surface area; and;
(iii) if the patient's initial platelet count is between $100 \times 10^9$/L and $200 \times 10^9$/L and the patient's platelet count before the subsequent treatment cycle is greater than or equal to $50 \times 10^9$/L, then the amount of tinostamustine or pharmaceutically acceptable salt thereof administered in the subsequent treatment cycle is 75-85 mg/m² (for example 80 mg/m²) based on free tinostamustine and the patient's body surface area; and
(iv) if the patient's initial platelet count is between $100 \times 10^9$/L and $200 \times 10^9$/L and the patient's platelet count before the subsequent treatment cycle is less than $50 \times 10^9$/L, then the amount of tinostamustine or pharmaceutically acceptable salt thereof administered in the subsequent treatment cycle is from 55-65 mg/m² (for example 60 mg/m²) based on free tinostamustine and the patient's body surface area; and
(v) if the patient's initial platelet count was less than $100 \times 10^9$/L and the patient's platelet count before the subsequent treatment cycle is greater than or equal to $50 \times 10^9$/L, then the amount of tinostamustine or pharmaceutically acceptable salt thereof administered in the subsequent treatment cycle is 54 mg/m² or lower (for example 45-54 mg/m² e.g. 50 mg/m²) based on free tinostamustine and the patient's body surface area; and
(vi) if the patient's initial platelet count was less than $100 \times 10^9$/L and the patient's platelet count before the subsequent treatment cycle is less than $50 \times 10^9$/L, then the amount of tinostamustine or pharmaceutically acceptable salt thereof administered in the subsequent treatment cycle is 44 mg/m² or lower (for example 35-44 mg/m² e.g. 40 mg/m²) based on free tinostamustine and the patient's body surface area.

The tinostamustine or a pharmaceutically acceptable salt thereof for use can be administered by any standard method. However, preferably the tinostamustine or pharmaceutically acceptable salt thereof is administered intravenously. The skilled person is aware as part of the common general knowledge of how to prepare solutions of tinostamustine or its salts for intravenous administration.

In particular, the tinostamustine or pharmaceutically acceptable salt thereof is administered over from 45-75 minutes, for example 50-70 minutes or 55-65 minutes e.g. 60 minutes.

In a fifth aspect, the present invention provides tinostamustine or a pharmaceutically acceptable salt thereof for use in the treatment of lymphoma or a T-cell malignant disease in a patient, wherein the tinostamustine or pharmaceutically acceptable salt thereof is administered:
intravenously;
at a dose of from 20-100 mg/m² based on free tinostamustine and the patient's body surface area, for example 95-105 mg/m², 75-85 mg/m², 55-65 mg/m², 45-55 mg/m² or 35-45 mg/m² (e.g. 100 mg/m²; 80 mg/m², 60 mg/m², 50 mg/m² or 40 mg/m²); and
over a period of time which is 45-75 minutes, for example 50-70 minutes or 55-65 minutes e.g. 60 minutes.

The tinostamustine can be used as free tinostamustine i.e. not as a pharmaceutically acceptable salt.

Alternatively, the tinostamustine can be used in the form of a pharmaceutically acceptable salt which is the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, oxalate, succinate, fumarate, tartrate, tosylate, mandelate, salicylate, lactate, p-toluenesulfonate, naphthalenesulfonate or acetate.

In particular, the tinostamustine is the acetate i.e the salt formed by reacting tinostamustine with acetic acid.

Tinostamustine and its salts can be prepared using methods which form part of the common general knowledge. In particular, reference is made to Example 6 of WO 2010/085377.

The tinostamustine or a pharmaceutically acceptable salt thereof is for use in the treatment of lymphoma.

In particular, the lymphoma is relapsed or refractory lymphoma.

Refractory lymphoma is disease that has not responded to initial treatment. Refractory disease may be disease that is getting worse or staying the same. Relapsed lymphoma is disease that has responded to treatment but then returned.

In particular, the tinostamustine or a pharmaceutically acceptable salt thereof is for use in the treatment of lymphoma which is:
Hodgkin lymphoma; or
non-Hodgkin lymphoma, for example NK/T-cell lymphoma (non-Hodgkin lymphoma that develops from natural killer cells or T lymphocytes), peripheral T-cell lymphoma (PTCLcutaneous T-cell lymphoma (CTCL) or anaplastic large cell lymphoma (ALCL).

In particular, the tinostamustine or a pharmaceutically acceptable salt thereof is for use in the treatment of a T-cell malignant disease which is T-cell-prolymphocytic leukemia (T-PLL).

The tinostamustine or a pharmaceutically acceptable salt thereof can be used as a monotherapy i.e. as the only therapeutic intervention.

Alternatively, the tinostamustine or the pharmaceutically acceptable salt thereof can be used in combination with one or more other compounds or therapies.

If the tinostamustine or pharmaceutically acceptable salt thereof is used in combination with one or more other compounds or therapies are administered concurrently, sequentially or separately.

In one embodiment the one or more other compounds are proteasome inhibitors, for example bortezomib, carfilzomib, marizomib, delanzomib (CEP-18770), oprozomib (ONX 0912), ixazomib (MLN-9708) or LU-102, and preferably bortezomib, carfilzomib and LU-102.

In particular, the one or more other compounds are glucocorticoids, for example dexamethasone, fluocinolone acetonide or prednisone e.g. dexamethasone.

In addition, the tinostamustine or a pharmaceutically acceptable salt can be used in combination with radiotherapy, for example wherein the radiotherapy is given at a dose of 1 to 5 Gy over 5-10 consecutive days, and preferably at 2 Gy over 5-10 consecutive days.

EXAMPLES

A phase 1 trial was carried out including a dose escalation study to investigate the safety, pharmacokinetic (PK) profiles and efficacy of tinostamustine (EDO-S101) in relapsed/refractory hematologic malignancies.

The patient had relapsed/refractory hematologic malignancies for which there are no available therapies.

Dose Escalation Levels

| Level | Dose | Administration time (infusion) | Schedule |
|---|---|---|---|
| 1 | 20 mg/m$^2$ | 1 hour | Every 21 days |
| 2 | 40 mg/m$^2$ | 1 hour | Every 21 days |
| 3 | 60 mg/m$^2$ | 1 hour | Every 21 days |
| 4 | 80 mg/m$^2$ | 1 hour | Every 21 days |
| 5 | 100 mg/m$^2$ | 1 hour | Every 21 days |
| 6 | 120 mg/m$^2$ | 1 hour | Every 21 days |
| 7 | One dose level below MTD | 45 minutes | Every 21 days |
| 8 | Two dose level below MTD | 30 minutes | Every 21 days |
| 9 | Escalation until maximum administered dose (MAD) or 150 mg/m$^2$ | 30 minutes | Every 21 days |

The assessment of dose-limiting toxicities (DLTs) was based on cycle 1 events alone. Toxicities were assessed regarding type and severity using the National Cancer Institute (NCI) Common Terminology Criteria for Adverse Events (CTCAE) version 4.03, June 2010. Toxicity data were collected for all patients throughout their time on study. Infusion site reactions were assessed using the Phlebitis Scale developed by the Infusion Nurses Society (2011).

DLTs, which were at least possibly related to study drug, were defined as:

Any Grade 3 or 4 non-hematologic toxicity (excluding alopecia and easily correctable electrolyte abnormalities);

Nausea, vomiting or diarrhoea that persists beyond 10 days despite aggressive symptomatic treatment;

Grade 4 neutropenia or thrombocytopenia lasting for 7 days or more;

Any grade 2 or more toxicity, but persist for over 3 weeks; and

Any toxicity resulting in a delay of the next dose administration (cycle 2 day 1≥14).

To ensure patients' safety, the stopping rules were implemented to the dose escalation stage of the study. If the following toxicity, which at least possibly related to the study drug, was observed in 66% or more patients treated at any dose level, the enrolment would have been put on hold to allow the sponsor to assess and address the risk:

Grade 2 increase of serum bilirubin level (>1.5-3.0×the upper limit of normal (ULN));

Grade 2 increase of serum creatinine (>1.5-3.0× baseline; >1.5-3.0×ULN); and

Grade 2 nervous system disorders excluding headache.

Other safety assessments included physical examinations, Eastern Cooperative Oncology Group (ECOG) performance status determinations, electrocardiograms (ECGs), pregnancy testing for women of childbearing potential, documentation of treatment-emergent adverse events (TEAEs), clinical laboratory evaluations including haematology, blood chemistry and urinalysis, vital signs, and documentation of concomitant medication usage.

PK Assessment

Plasma samples were collected to determine the concentrations of tinostamustine and its metabolites (labelled M2 and M8) by a method fully validated according to the relevant guidelines. The PK profiles of tinostamustine in plasma were assessed in each patient in the escalation stage of the study, in cycle 1 only.

Tumour Assessment

Response to treatment included evaluation of overall response rate (patients with a CR plus patients with a PR), clinical benefit (CB) rate (patients with CR plus patients with PR plus patients with stable disease (SD)), progression free survival, and overall survival according to the relevant response criteria.

Independent Data Monitoring Committee (IDMC)

A Data Safety Monitoring Committee (DSMC) was established for this study. It consisted of four members, two independent haematologist-oncologists experienced in clinical trials, (one being nominated as chairman), a physician nominated by the sponsor and a statistician. The decisions to escalate to the next dose level occurred after each cohort patients' data were discussed with the DSMC.

Dose Escalation Stage Summary

The study had a 3+3 design, in patients with relapsed/refractory hematological malignancies (HM). In these studies, three patients are initially enrolled into a given dose cohort. If there is no DLT observed in any of these subjects, the trial proceeds to enroll additional subjects into the next higher dose cohort. If one subject develops a DLT at a specific dose, an additional three subjects are enrolled into that same dose cohort. Development of DLTs in more than 1 of 6 subjects in a specific dose cohort suggests that the MTD has been exceeded, and further dose escalation is not pursued.

The dose escalation phase included 46 patients enrolled across nine different cohorts. Among all 46 patients, 31 (69%) have discontinued from the study, with the reason for discontinuation being progressive disease (PD) for 17 (38%) patients, adverse events (AE) for 13 (29%) patients, and 1 (2%) patient discontinued from the study because of an "other" reason.

| Disease | N | Dosing Cohort: mg/m$^2$/infusion time (mins) | | | | | | | | |
|---|---|---|---|---|---|---|---|---|---|---|
| | | 20/60 | 40/60 | 60/60 | 80/60 | 100/60 | 120/60 | 80/45 | 60/30 | 80/30 |
| Multiple Myeloma | 19 | 0 | 2 | 1 | 1 | 7 | 0 | 5 | 3 | 0 |
| Non-Hodgkin lymphoma | 17 | 3 | 0 | 2 | 2 | 1 | 2 | 3 | 4 | 0 |
| Hodgkin lymphoma | 10 | 0 | 1 | 0 | 0 | 0 | 4 | 2 | 2 | 1 |
| Total | 46 | 3 | 3 | 3 | 3 | 8 | 6 | 10 | 9 | 1 |

Six cycles of treatment were planned at each dose level. Patients who benefited from treatment were allowed to receive more cycles. Patients who did not respond to therapy and those who developed early toxicity were treated with one to three cycles.

Of the 46 patients enrolled, 27 of the patients have lymphoma (Hodgkin and non-Hodgkin) and 19 patients have multiple myeloma (MM).

Initially, stage 1 of the study enrolled 20 patients with HM, including 9 patients with lymphoma and 11 patients with MM, into a total of 5 ascending dose cohorts as follows:

20 mg/m² over 1 hour (HM20/60 cohort; N=3)
40 mg/m² over 1 hour (HM40/60 cohort; N=3)
60 mg/m² over 1 hour (HM60/60 cohort; N=3)
80 mg/m² over 1 hour (HM80/60 cohort; N=3)
100 mg/m² over 1 hour (HM100/60 cohort; N=8)

The dose of 100 mg/m² administered over 60 minutes was determined to be the maximum tolerated dose (MTD) in the subset of patients with MM (N=11). Although no dose-limiting toxicities (DLTs) occurred in cycle (C) 1 in this dose level, three patients experienced Grade 3 and 4 thrombocytopenia in C2 and C3, leading to the patients' withdrawal from the study.

Subsequently, cohorts with tinostamustine at lower doses administered over shorter infusion times of 45 minutes and 30 minutes were initiated in patients with MM. A total of 8 patients with MM were enrolled in 2 cohorts, as follows:

60 mg/m² over 30 minutes (MM60/35 cohort; N=3)
80 mg/m² over 45 minutes (MM80/45 cohort; N=5)

Patients with lymphoma, as per protocol, were enrolled in a separate cohort with tinostamustine 120 mg/m² administered over 1 hour. Two out of six patients experienced DLTs. Consequently, 120 mg/m² administered over 1 hour was determined as the MAD for the treatment of lymphoma subpopulation and the dose of 100 mg/m² determined as the MTD. Tinostamustine at lower doses administered over shorter infusion times of 45 and 30 minutes were initiated in patients with lymphoma. A total of 18 patients with lymphoma were enrolled in 4 lymphoma cohorts, as follows:

120 mg/m² over 1 hour (LYM120/60 cohort; N=6)
80 mg/m² over 45 minutes (LYM80/45 cohort; N=5)
60 mg/m² over 30 minutes (LYM60/30 cohort; N=6)
80 mg/m² over 30 minutes (LYM80/30 cohort; N=1)

The recruitment to the last cohorts of 80 mg/m² over 30 minutes was stopped due to the high $C_{max}$. High $C_{max}$ and increased hematotoxicity was also observed in the phase 1/2 solid tumour study with tinostamustine in 30 minutes infusion time. Therefore, the one hour infusion time was selected, and the determination of MTD for shorter infusion was terminated.

Safety
Overview

Among all 46 patients, 42 (91%) experienced at least one treatment-emergent adverse event (TEAE), with at least one TEAE considered by the investigator to be study drug-related for 38 patients. The most common types of TEAEs were blood and lymphatic system disorders (25 patients; 54%), gastrointestinal (GI) disorders (24 patients; 52%), and general disorders and administration site conditions (23 patients; 50%).

Overall, the most common individual TEAEs were hematologic abnormalities, including thrombocytopenia/platelet count decreased (24 patients (52%)), anaemia (18 patients (39%)), nausea and neutropenia/neutrophil count decreased (each 13 patients (29%)) and leukopenia/white blood cell count (WBC) decreased (10 patients (21%)). All other TEAEs occurred in <20% of patients.

Overall, 29 (63%) patients experienced a grade 3 or 4 TEAE, with 60% (28 patients) and 28% (13 patients) experiencing at least 1 grade 3 and grade 4 TEAE, respectively. No patient experienced a TEAE with an outcome of death (i.e., a grade 5 TEAE). The most common individual grade 3/4 TEAEs were hematologic abnormalities, including thrombocytopenia (18 patients (39%)), neutropenia/neutrophil count decreased (13 patients (29%)), anemia (10 patients (22%)), leukopenia/WBC decreased (seven patients (15%)), and lymphopenia (4 patients (8.6%)). All other grade 3/4 TEAEs occurred in one or two patients only.

Infusion-site phlebitis events were not common, with only one (2%) patient experiencing this type of event. Eight (18%) patients experienced at least 1 serious adverse event (SAE), including febrile neutropenia and sepsis (each 2 patients (2%)) and dyspnea, hypersensitivity, osteomyelitis, pleural effusion, pneumonia, and thrombocytopenia (each one patient (2%)). Of these events, dyspnea and pleural effusion were considered by the investigator to be unrelated to study drug. The remaining events were considered study drug-related.

11 (23%) patients discontinued study drug because of a TEAE. The only TEAEs leading to study drug discontinuation for >1 patient were thrombocytopenia (7 patients (15%)) and neutropenia (two patients (4%)). All other TEAEs leading to study drug discontinuation were reported for one (2%) patient only and included anaphylactic reaction, febrile neutropenia, hypersensitivity, pleural effusion, and pruritus. A summary of the most common (overall incidence>10%) TEAEs overall, by dose regimen, is as follows, wherein patients are counted if they suffered at least one of the class of TEAE (using the MedDRA preferred term):

| Adverse event | Patients (N = 46) |
| --- | --- |
| TEAE | 42 (91.3) |
| Treatment-related* TEAE | 38 (82.6) |
| Grade 3 TEAE | 28 (60.8) |
| Grade 4 TEAE | 13 (28.2) |
| Infusion site phlebitis | 1 (2.1) |
| SAE | 8 (17.4) |
| TEAE leading to early study discontinuation | 11 (23.9) |
| TEAE with outcome of death | 0 (0) |

*Treatment-related TEAE are AEs recorded as relationship possible, probable or definite.

Haematology

The principle toxicities associated with tinostamustine have been hematologic abnormalities, primarily thrombocytopenia/platelet count decreased (hereafter referred to as thrombocytopenia), anaemia, neutropenia/neutrophil count decreased (hereafter referred to as neutropenia), and leukopenia/WBC decreased (hereafter referred to as leukopenia). Across cohorts 20/60 to 120/60, a dose relationship was apparent with regard to the incidence of these common hematologic abnormalities, with the incidence increasing with increasing dose.

Thrombocytopenia

Overall, 52% (24/46) of patients experienced at least 1 incidence of thrombocytopenia. Across cohorts 20/60 to 120/60, the incidence of thrombocytopenia generally increased with increasing dose. Thrombocytopenia was also common when tinostamustine was administered over a shorter infusion period, with an incidence of 47% (9/19) across all cohorts at which tinostamustine was administered over 30 or 45 minutes. When tinostamustine was administered over 60 minutes, the incidence of thrombocytopenia was 58% (15/26). Thrombocytopenia was grade 3 or 4 in intensity for 18 of these 24 patients (incidence 40% overall). Again, across cohorts 20/60 to 120/60, a dose relationship was apparent with regard to the incidence of grade 3/4 thrombocytopenia, with an incidence of 71% (7/14) at doses of 100 or 120 mg/m² versus 8% (1/12) at doses of 20 to 80 mg/m². For one (2%) patient (HM120/60 cohort), thrombocytopenia (grade 3) was serious and also led to study discontinuation. All other cases of thrombocytopenia were non-serious. Thrombocytopenia was generally persistent. In total, thrombocytopenia led to study drug and/or study discontinuation for 9 (19%) patients, 7 of whom received tinostamustine at a dose of 100 or 120 mg/m² over 60 minutes, making it the most common TEAE leading to discontinuation.

Anaemia

Overall, 18 (39%) patients experienced at least one incidence of anaemia. Across cohorts 20/60 to 120/60, the incidence of anaemia generally increased with increasing dose, with an incidence of 64% (9/14) at doses of 100 or 120 mg/m² versus 25% (3/12) at doses of 20 to 80 mg/m². Mitigation of anaemia was not apparent with lower tinostamustine doses over a shorter infusion time, with an incidence of 37% (7/19) across all cohorts at which tinostamustine was administered over 30 or 45 minutes. Anaemia was grade 3 or 4 in intensity for 10 (22%) patients overall, again, with a higher incidence at doses of 100 or 120 mg/m² (36% (5/14)) than at doses of 20 to 80 mg/m² (8% (1/12)). All cases of anaemia were non-serious, and none led to study or study drug discontinuation.

Neutropenia

Overall, 13 (28%) patients experienced at least one incidence of neutropenia, with all 13 patients experiencing grade 3 or 4 neutropenia. Across cohorts 20/60 to 120/60, the incidence of neutropenia was higher at doses of 100 or 120 mg/m² (50% (7/14)) than at doses of 20 to 80 mg/m² (25% (3/12)). Neutropenia was less common with tinostamustine was administered over shorter infusion times (16% (3/19)). All cases of neutropenia were non-serious. Two patients discontinued study drug and/or the study because of neutropenia.

Leukopenia

Overall, 10 (22%) patients experienced at least one incidence of leukopenia, with at least one such event being grade 3 or 4 in intensity for 7 (16%) patients. Across cohorts 20/60 to 120/60, the incidence of leukopenia was higher at the higher doses of 100 or 120 mg/m² (36% (5/14)) than at doses of 20 to 80 mg/m² (17% (2/12)). The incidence of leukopenia was 16% (3/19) when tinostamustine was administered over 30 or 45 minutes compared to 27% (7/26) when administered over 60 minutes. No patient discontinued study drug or the study because of leukopenia.

Biochemistry

Treatment-emergent shifts to grade 3 or 4 clinical chemistry abnormalities were not common. Only one (2%) patient with normal or grade 1 or 2 values at baseline experienced a treatment-emergent grade 4 clinical chemistry abnormality, hyperuricemia. One (2%) patient each with normal or grade 1 or 2 values at baseline experienced a treatment-emergent shift to grade 3 aspartate aminotransferase increased and grade 3 hypoalbuminemia. Clinical chemistry TEAEs are summarized as follows (using MedDRA preferred term):

| MedDRA preferred term | All Patients (N = 46) n (%) |
| --- | --- |
| Blood potassium decreased/hypokalaemia | 5 (10.8) |
| Blood creatinine increased | 4 (8.6) |
| C-reactive protein increased | 2 (4.3) |
| Blood alkaline phosphatase increased | 1 (2.1) |
| Blood magnesium decreased | 1 (2.1) |
| Hyperuricemia | 1 (2.1) |
| Hyperglycaemia | 1 (2.1) |

Individual clinical chemistry TEAEs were also not common. The only clinical chemistry TEAEs occurring in >1 patient were blood potassium decreased/hypokalemia (5 patients (11%)) and blood creatinine increased (4 patients (9%)). In addition, two (4%) patients experienced C-reactive protein increased. All but one clinical chemistry TEAE were non-severe. One (2%) patient experienced grade 3 hyperuricemia, with this event considered by the investigator to be unrelated to study drug.

Given the low overall incidence of clinical chemistry abnormalities, any dose relationship could not be ascertained.

DLTs and MTD

DLTs occurred in the dose cohort of 120/60, in the following patients:

Grade 4 thrombocytopenia lasting for 7 days or more; and
Prolonged thrombocytopenia/toxicity resulting in the delay of the next dose administration (C2 day 1≥14 days)

The dose of 100 mg/m² was determined as MTD for lymphoma and multiple myeloma patients Cardiac Safety No patient had a treatment-emergent ECG abnormality that was indicated to be clinically significant.

One patient had a treatment-emergent corrected QT interval by Fredericia (QTcF interval)>500 msec.

One subject in the MM 80/45 cohort, who had a screening QTcF of 423 msec, had a prolonged QTcF interval of 677 msec at the discontinuation visit, three weeks after his only study drug dose on day 1 of C1. A non-specific T wave abnormality was evident in the anterior leads at that time. The QTcF interval prolongation was reported as a TEAE (MedDRA preferred the term electrocardiogram QT interval prolonged), with this event assessed by the investigator as grade 2 in intensity and possibly related to study drug. No further follow-up was available. The patient subsequently died as a result of his underlying disease.

No other patient had an ECG abnormality reported as a TEAE.

Overall, the incidence of cardiac disorders was relatively low (11% (5/45)), with the only cardiac disorder reported for >1 patient being tachycardia (2 patients; 4%). Only 1 (2%) patient experienced a cardiac disorder that was considered by the investigator to be study drug-related, grade 1 palpitations. All cardiac disorders were grade 1 or 2 in intensity and non-serious and none led to study drug discontinuation.

Pharmacokinetics and Pharmacokinetic (PK)/Pharmacodynamic (PD) Safety Modelling

The observed toxicities during the escalation stage of the trial over 20 to 120 mg/m² at infusion times 60, 45 and 30 minutes, which appeared to be critical for dose and schedule, were haematological only. Tinostamustine impacted on peripheral blood lymphocytes, neutrophils and platelets by reducing cell counts over the treatment cycles.

Surprisingly, although lymphocytes were considered the target cell population, the reduction of platelets became dose-limiting.

The key pharmacokinetic parameters, the relationship between the pharmacokinetics and the impact on peripheral blood cells were analyzed. A PK model was developed to describe and predict the dose-haematological toxicity relationship in a wider population.

Pharmacokinetics (PK)

Patients of all cohorts and over all dose levels were sampled according to the following schedule: 0.5 hours prior to dose administration, and at 15, 30 and 45 minutes and 1, 1.25, 1.50, 2, 3, 8, 24, 48 and 72 hours from the start of tinostamustine infusion. Plasma samples were collected according to the Laboratory Manual for the determination of tinostamustine and metabolites M2 and M8 concentrations using a method fully validated according to the relevant guidelines.

The following PK parameters were assessed either by using a non-compartmental analysis or were obtained through the population PK model:

$C_{max}$, AUC, and $T_{max}$ for each dose cohort and infusion time;
Terminal half-life;
Volumes of distribution;
Linearity and variability over the dose range; and
Impact of shorter infusion time from 60 to 45 and 30 min for a given dose on safety.

The sample analysis showed tinostamustine parent compound being the main active component in plasma and metabolites M2 and M8 only made up for <1% and <10%, respectively. Therefore only the tinostamustine parent compound was considered for PK data for analyses and conclusions. The following table summarizes the main exposure parameters over the studied dose range and infusion time on day one:

| Dose (mg/m²) | Infusion time (minutes) | Mean (SD) | | | No. patients |
|---|---|---|---|---|---|
| | | $C_{max}$ (ng/mL) | AUC (h · ng/mL) | $T_{max}$ (min) | |
| 20 | 60 | 241 (20) | 193 (30) | 48 (12) | 3 |
| 40 | 60 | 1162 (599) | 932 (425) | 24 (18) | 3 |
| 60 | 30 | 1724 (1416) | 627 (491) | 18 (6) | 9 |
| 60 | 60 | 640 (85) | 592 (75) | 60 (0) | 3 |
| 80 | 45 | 1277 (319) | 794 (151) | 24 (6) | 5 |
| 80 | 60 | 1064 (678) | 902 (653) | 48 (24) | 3 |
| 100 | 60 | 1955 (875) | 1657 (523) | 42 (24) | 6 |
| 120 | 60 | 1773 (507) | 1638 (578) | 48 (12) | 6 |

The median PK profiles over a dose range from 20 to 100 mg/m² and at different rates of infusion are shown in FIG. 1.

Figure 2:
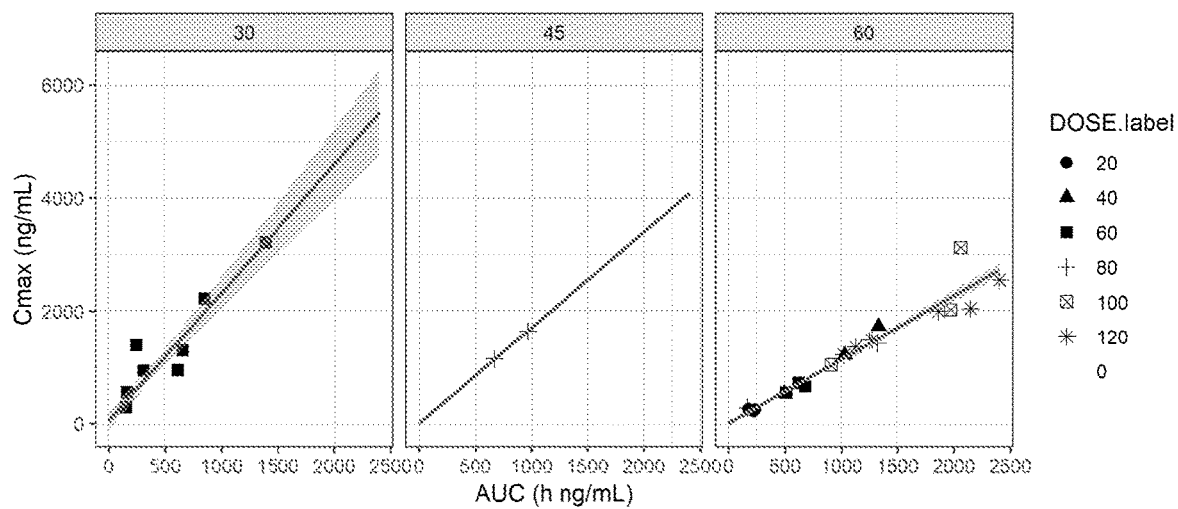
FIG. 2 shows the individual day one tinostamustine $C_{max}$ versus $AUC_{0-8\ hours}$ linear regression fit.

FIG. 2 shows that the decrease of the infusion time from 60 to 30 minutes doubled the $C_{max}$ for the same AUC. However, the $C_{max}$ was variable in particular in the 60 mg/m² over 30 minutes infusion group, where the standard deviation was the largest at 1416 ng/mL. The time to maximum concentrations was achieved at the end of infusion, between 45 and 60 minutes for the 60 minute infusion, and at around 30 minutes for the shorter infusions. Decline from peak concentration occurred in a bi-phasic manner.

A compartmental population PK analysis of tinostamustine was conducted to characterize its concentration-time profiles and its dependency on patient factors. For the analysis, the 24 hours plasma concentrations of tinostamustine at day one from 36 patients was used from whom the data was available. The concentration-time profiles were best described with a two-compartmental model with first order clearance from the central compartment. The model analysis showed that the PK of tinostamustine was dose-linear in the investigated dose range of 20 to 120 mg/m² and for infusion times of 30 to 60 minutes. Further, it was found that the PK did not depend on patient age, body weight or gender. The peripheral volume of distribution was 11.5 L, which was comparable to the interstitial water volume. The between patient variability in the clearance expressed as the coefficient of variation (% CV) was average at 27% and for the central volume of distribution high at 65%, and the large variability in the central volume is likely a result of the observed variability in $C_{max}$:

| Parameter | Estimation |
|---|---|
| Central volume of distribution | 20.6 L (% CV = 65%) |
| Peripheral volume of distribution | 11.5 L |
| Clearance | 6.75 L/day (% CV = 27%) |
| α half-life | 27 minutes |
| β half-life | 3.6 hours |

PK/PD Safety Modelling

The obtained exposure parameters ($C_{max}$ and AUC) and PK profiles from individual patients and the respective haematological laboratory data were collected over the treatment duration and analysed regarding the relationship to peripheral blood cell counts (lymphocytes, neutrophils, platelets).

Materials and Methods

The effect of tinostamustine on blood cell counts was studied by investigating the relationship between the nadir of the blood cell counts and the tinostamustine nominal dose in mg/m², $C_{max}$ or $AUC_{0-24}$ hours (predictors). The nadir was defined as the lowest blood cell count observed after the first administration. The nadir was extracted irrespective of the treatment duration, thus, the analysis data set included patients who received only one dose and patients who received multiple treatment cycles with tinostamustine. The baseline blood cell count, which was the count before the first administration, was included in the analysis as the cell count at dose, $C_{max}$ or AUC equal to 0. Thus, it was assumed that the baseline blood cell count was the effect level without treatment with tinostamustine. With an exploratory analysis all observations each predictor-nadir relationship was fitted with a least-squares method in R. The dose-nadir relationship was further investigated with a non-linear mixed effects approach. The advantage of the non-linear mixed effects approach compared to the exploratory analysis was that different external and patient factors could be investigated at the same time and the between patient variability can be described. The infusion time, type of blood cancer (Hodgkin lymphoma, non-Hodgkin lymphoma, follicular lymphoma (FL), multiple myeloma, or unknown), blood cell count at baseline and the patients' age, bodyweight and sex were tested as factors on the dose-blood cell count nadirs relationship. The effects were tested at a significance level of p=0.01. The dose-nadir relationships were described either with a sigmoid curve:

$$\text{Cell count} = \text{Baseline}\left(1 - \frac{D^Y}{EC50^Y + D^Y}\right)$$

or an exponential curve:

$$\text{Cell count} = \text{Baseline} \cdot e^{D \cdot \log(2)/EC50}$$

where D was the nominal dose of tinostamustine in mg/m². Based on the above baseline parameters, EC50 were estimated for platelets, neutrophils and lymphocytes for each individual patient assuming that individual parameters would be log-normally distributed. The parameter estimation was done with Monolix2018R1. The analysis included 46 patients for which the treatment information and the blood cell counts were available. Four patients were excluded from the analysis because of disease progression.

The non-linear mixed effects model describing the dose-nadir relationship was used to simulate dose-nadir response curves and to predict the percent patients with grade 3 and grade 4 AE for different doses. For simulations, the patient factors from the patients from study S1001 were used to generate a population via re-sampling of the blood cell counts at baseline. This ensured that the correct correlations between the different blood cell counts where maintained. The 46 patients were resampled 40 times producing a total of 1400 patients from which the statistics was computed. The AE grades used for the analysis were defined as follows:

| AE grade | 2 | 3 | 4 |
|---|---|---|---|
| Platelets ($10^9$/L) | 75 | 50 | 25 |
| Neutrophils ($10^9$/L) | 1.5 | 1 | 0.5 |
| Lymphocytes ($10^9$/L) | 0.8 | 0.5 | 0.2 |

Pharmacokinetic Metrics and the Relationship to Peripheral Blood Cell Counts

It became apparent through the escalation stage that rising doses of tinostamustine caused a reduction of peripheral blood cell counts, namely lymphocytes, neutrophils and platelets. It was therefore analysed if blood cell compartments had a differential sensitivity to tinostamustine and which of the PK metrics ($C_{max}$, AUC or dose) would be best correlated and able to predict effects of various tinostamustine doses.

Figure 3:
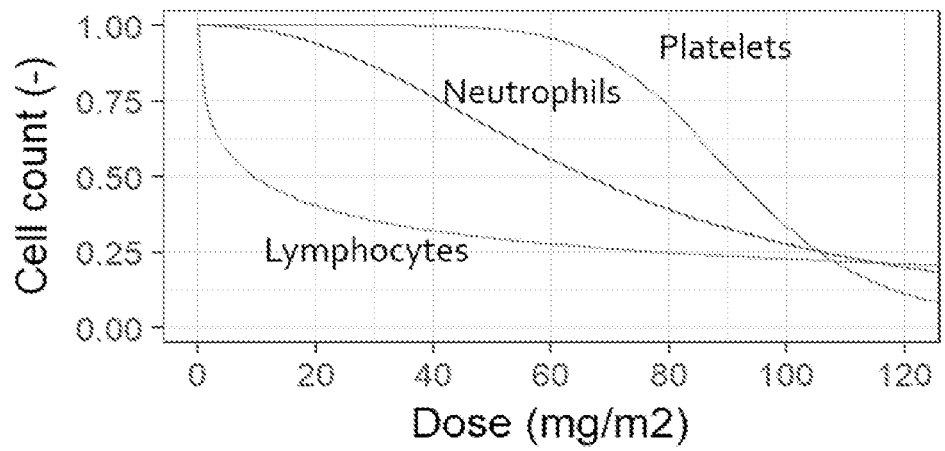
FIG. 3 shows the relative effect on lymphocyte (LYM), neutrophil (NEU) or platelet (PLT) counts versus dose from the exploratory analysis.

The exploratory analysis confirmed the correlation of rising exposure or doses with the decline in blood cells of all three compartments. There was no significant difference if $C_{max}$, AUC or the nominal dose was used but using the dose as the metric, the effects of the dose lead to the best separation of the impact on lymphocytes, neutrophils and platelets, see FIG. 3. The analysis of $C_{max}$ and AUC versus cell count has not been shown.

Figure 4:
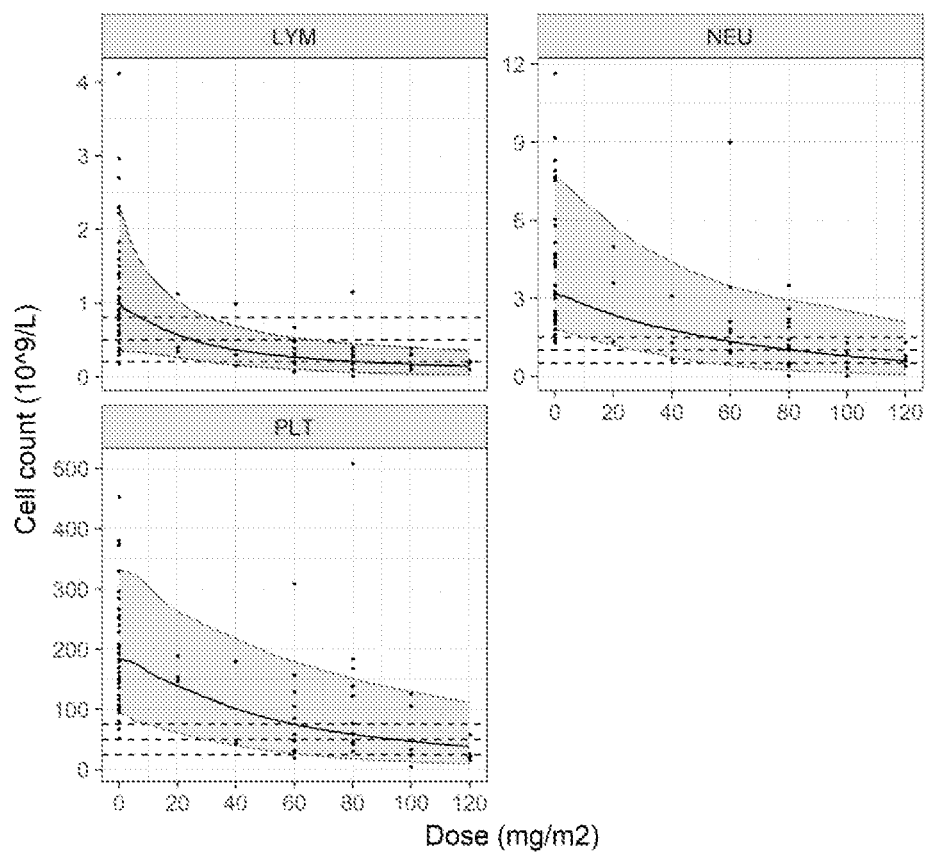
FIG. 4 shows the model fit of the blood cell counts.

The respective nadir data points were fitted with a non-linear mixed effects model to determine the respective EC50 values of tinostamustine doses on peripheral blood cell counts. The data suggested that tinostamustine had an early and profound impact on lymphocytes, followed by neutrophils and finally platelets, see FIG. 4 wherein the dots represent observed blood cell counts, the black line represents predicted median nadir, the shaded area represents the 80th percentile of the predicted nadir, and the dashed lines show grade 2, 3 or 4 AEs. The effects on the lymphocyte compartment were regarded as an effect on the target cell population as the diseases investigated in this trial were all arising from lymphocytes.

Lymphocytes were the most sensitive cell population with an estimated EC50 at a dose of 28.3 mg/m² (dose required to reduce the cell count by 50%). Neutrophils were the second most sensitive with an EC50 of 49.1 mg/m². As reported in the safety section above, there was no increase in infections or a high incidence in neutropenic fever observed. Platelets were the most robust cell compartment with an EC50 of 55.5 mg/m². The decline in platelets was considered dose defining because recovery exceeded the length of the treatment cycle or was a DLT (120 mg/m²). The different sensitivities also translated into different dose levels that would result in a grade 3 AE in 50% of the treated patients. For lymphocytes, a dose of 25 mg/m² was predicted to result in grade 3 AE in 50% of the patients. For neutrophils, the predicted dose level was 80 mg/m² and for platelets, 95 mg/m². The estimated model parameters and predicted dose that would result in a grade 3 AE related to the respective blood cell type in 50% of the patients are as follows:

| Cells | Baseline ($10^9$/L) | EC50 (mg/m²)(% CV) | Dose for grade 3 AE (mg/m²) in 50% of patients |
|---|---|---|---|
| Platelets | 192 | 55.5 (72%) | 95 |
| Neutrophils | 3.25 | 49.1 (70%) | 80 |
| Lymphocytes | 1 | 28.3 (40%) | 25 |

Other Metrics Influencing Peripheral Blood Cell Counts

Figure 5:
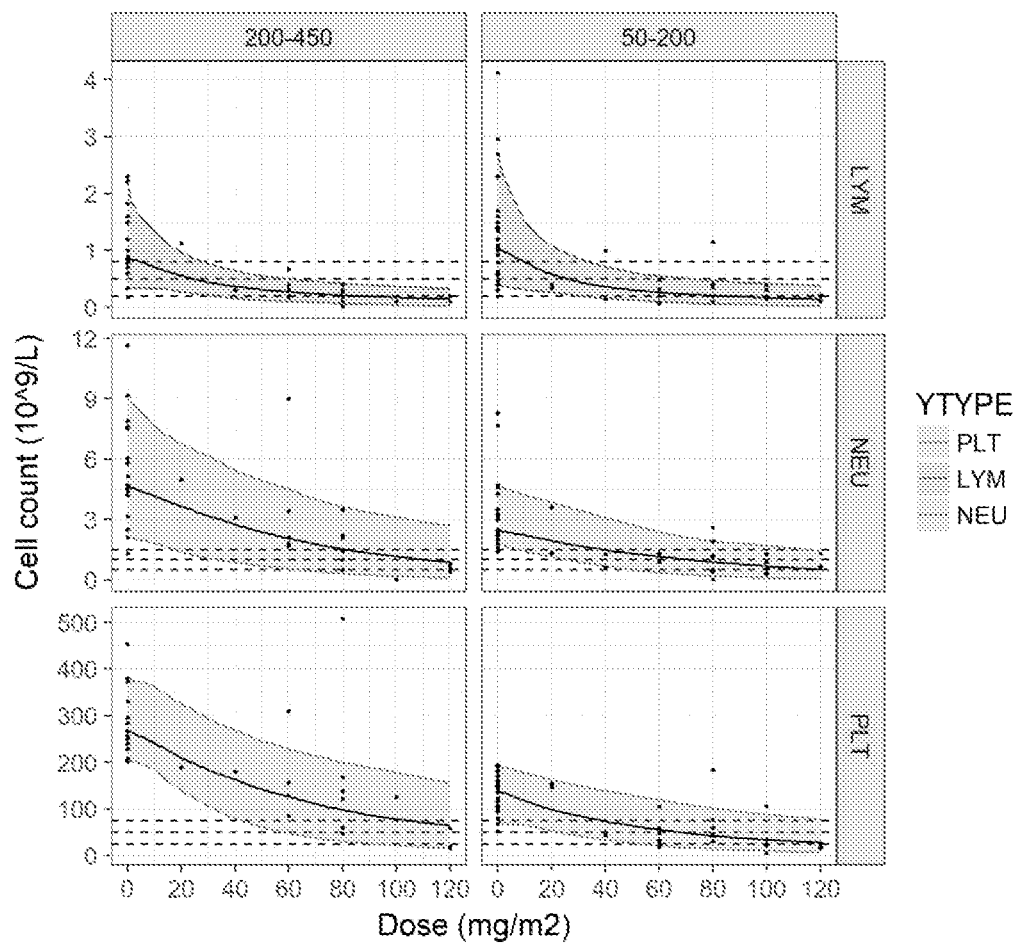
FIG. 5 shows the simulated dose-nadir relationships for patients with platelet cell counts ranging from 50-200 and 200-450 $10^9$/L.

The trial recruited heavily pre-treated and elderly patients, which often based on age and prior therapy have a limited capacity to regenerate peripheral blood cells. The PK, haematology laboratory and demographic patient factors were therefore analyses as to whether there was a relationship to the observed haematological toxicity. The factors taken for analysis were age, gender, and underlying malignancy. The approach was to use a mixed-effects model to identify possible relationships and statistical significant covariates. The results showed no impact of age, sex and underlying disease or infusion time. The one determining factor to determine grade 3 or 4 platelet decrease was the platelet count at the start of therapy. The relation is shown in FIG. 5.

Dose Tolerability and Platelet Counts at Baseline

As it became apparent that the platelet count at baseline is determining the tolerability of a given dose, we looked at the platelet count at baseline distribution and did further simulations with various cut-off platelet counts in order to understand if there were patient groups who would best be treated with different doses.

The data set for analysis comprised of 42 patients treated over the dose range from 20 to 120 mg/m². Four patients were excluded because disease progression in the bone marrow confounded the effect of tinostamustine and a drug effect on platelet counts could not be established.

Figure 6:
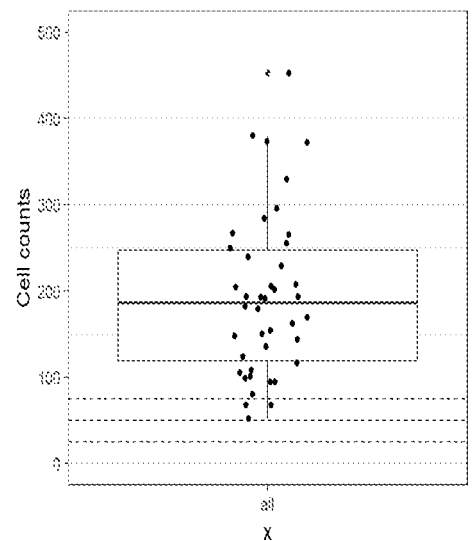
FIG. 6 shows a boxplot showing the median, 25% and 75% percentile of platelet counts at baseline.
Figure 7:
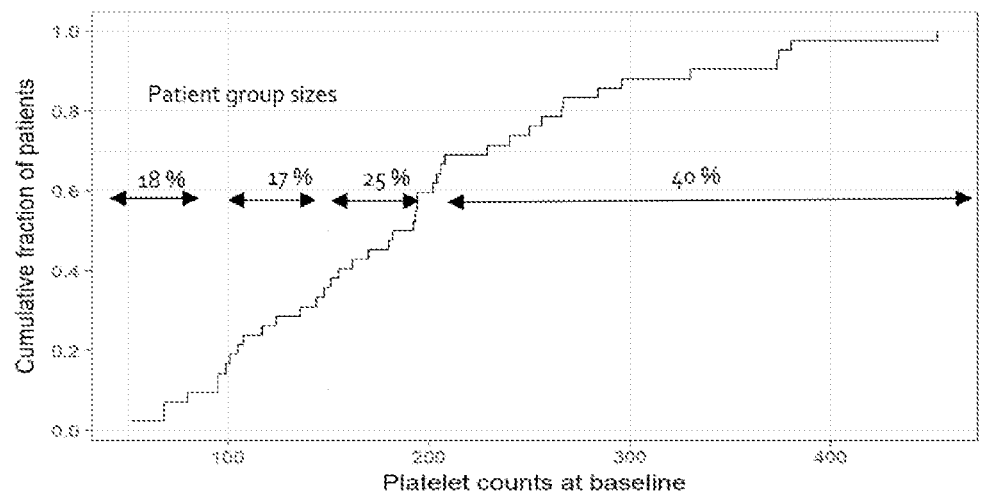
FIG. 7 is a cumulative curve of platelet count at baseline and respective proportion of patients per group.
Figure 8:
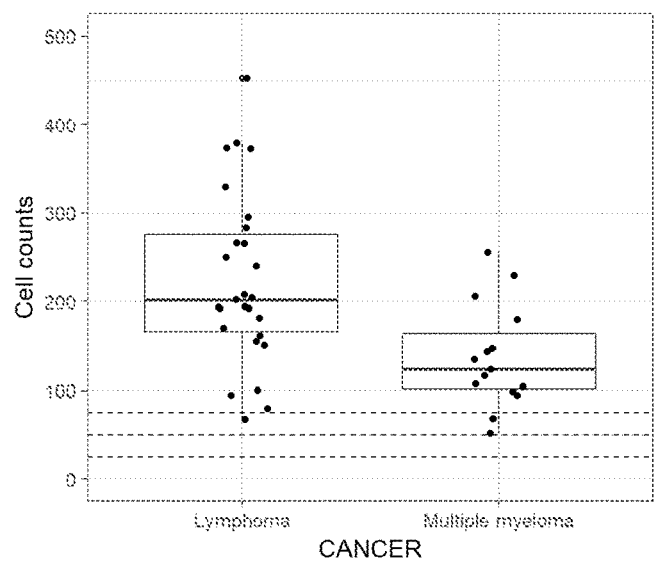
FIG. 8 is a boxplot of median, 25% and 75% percentile platelet counts at baseline per underlying disease.

The distribution of platelet counts at baseline is shown in FIG. 6. The median platelet count in the analysis population is 180×10⁹/L and only few patients are in the range of 100×10⁹/L. The cumulative curve for platelet count at baseline in FIG. 7 shows indeed that only 18% of patients are at 100×10⁹/L or lower, a population which was considered most vulnerable to platelet loss.

Platelet counts were also looked at per underlying disease as it was hypothesized that multiple myeloma patients may have entered the study with lower counts because the disease sits in the bone marrow and patients generally had a higher number of previous treatment. The median counts between lymphoma patients (200×10⁹/L) were substantially higher than for patients with multiple myeloma (median 120×10⁹/L). However, the underlying disease is not regarded a relevant factor to determine a tolerable dose.

Figure 9:
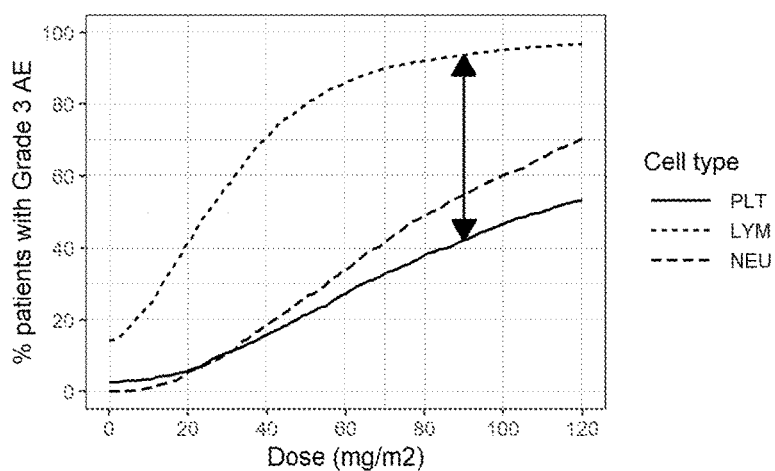
FIG. 9 shows the reference dose for 20% likely grade 4 thrombocytopenia and 90% grade 3 lymphocytopenia.
Figure 9:
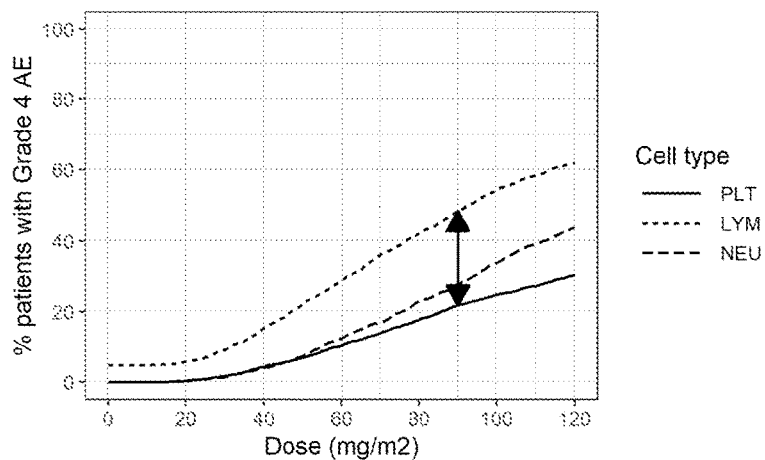

For the simulations and in order to support the selection of a RP2D, a few assumptions were made. We set the rate of grade 4 thrombocytopenia for a given dose at not higher than 20% and we defined a 90% chance for a grade 3 lymphocytopenia as a surrogate for sufficient efficacy. The reference case was the dose over the entire analysis population (all platelet counts) for these criteria, see FIGS. 9a and b. The reference dose for this scenario was determined to be 90 mg/m².

Simulations were performed against the reference group by dividing the analysis population into two groups with different cut-off counts of platelet counts (×10⁹/L):
Case 1 two groups: 50-100 and 100-450;
Case 2 two groups: 50-150 and 150-450; and
Case 3 two groups: 50-200 and 200-450;

and into one scenario where we analysed a case where three groups were formed.

Case 4 three groups: 50-100, 100-200 and 200-450.

The simulation by dividing patients into three groups according to their platelet counts at baseline lead to the following results in term of tolerable doses which would represent a 20% risk to experience a grade 4 thrombocytopenia and a 90% chance to have a grade 3 lymphocytopenia:

| Case | Groups (cells $10^9$/L) | Percent patients | Dose (mg/m$^2$) | Grade 4 PLT AE rate At 90 mg/m$^2$ | Grade 4 PLT AE rate At dose | Grade 4 LYM AE rate At 90 mg/m$^2$ | Grade 3 LYM AE rate At dose |
|---|---|---|---|---|---|---|---|
| 4 | 50-100 | 18 | 50 | 45% | 20% | 99% | 95% |
|   | 100-200 | 42 | 95 | 20% | 20% | 90% | 90% |
|   | 200-450 | 40 | 120+ | 10% | 20% | 95% | 98% |

The simulations revealed that the lowest dose, which can be expected to have a meaningful impact on lymphocytes is 50 mg/m$^2$. On the other end, patients with platelet counts above 200×10$^9$/L can be treated with the highest dose explored in the escalation stage, namely 120 mg/m$^2$. The following observations were also taken into account for the recommendation of cut-off counts and the respective dose:
 i. Patients with a platelet count of 100×10$^9$/L or lower are the most vulnerable in terms of platelet loss and should be treated with the dose just effective and having the least impact on platelet counts.
 ii. Patients with multiple myeloma rarely had platelet counts of more than 200 10$^9$/L and therefore did not tolerate a dose of 100 mg/m$^2$.
 iii. Patients with lymphoma generally had higher platelet counts and 1 patient with refractory
HL was treated with 120 m/m$^2$ over 6 cycles and achieved a CR.

As a result of the simulations of case 4 and additional observations as above, it is recommended to set the following doses given once every 3 weeks per category of platelet counts at baseline:
 i. Dose for platelet counts of 100×10$^9$/L or lower is 50 mg/m$^2$ over 60 minutes infusion, d1 q3w (i.e. day 1, every third week).
 ii. Dose for platelet counts from 100-200×10$^9$/L is 80 mg/m$^2$ over 60 minutes infusion, d1 q3w.
 iii. Dose for platelet counts from 200×10$^9$/L or higher is 100 mg/m$^2$ over 60 minutes infusion, d1 q3w.

PK Summary

The PK of tinostamustine over a dose range of 20-120 mg/m$^2$ given over 60 minutes infusion time is linear. The main toxicity is haematological with a decline in peripheral blood lymphocytes, neutrophils and platelets. The decline in platelets is dose limiting with either causing a prolonged recovery time exceeding the treatment cycle observed in multiple myeloma patients at 100 mg/m$^2$, or as a DLT in cycle 1 in patients with lymphoma (120 mg/m$^2$).

The peripheral cell compartments show a differential sensitivity to tinostamustine with lymphocytes being most sensitive and platelets most robust, but showing the most rapid decline at higher doses.

The further modelling of the dose and thrombocytopenia relationship revealed the sole factor to predict grade 3 or 4 thrombocytopenia was the platelet count at the start of therapy. Other factors such as age, gender, underlying disease or infusion time appeared to have no influence on thrombocytopenia.

Simulations with patient groups and various cut-offs for platelets counts showed that the dose levels to be likely well tolerated seemed to fit best to three patients categories:

Patients with platelet counts of 100×10$^9$/L or lower would receive 50 mg/m$^2$ over 60 minutes infusion.

Patients with platelet counts of higher than 100 and lower than 200×10$^9$/L would receive 80 mg/m$^2$ over 60 minutes infusion, Patients with platelet counts of 200×10$^9$/L or higher would receive 100 mg/m$^2$ over 60 minutes infusion.

Schedule: i.v. once every 3 weeks

Signals of Efficacy

Response for all HM

Among all 46 patients, the overall response rate (ORR) was 28% (13 patients) and the clinical benefit rate (CBR) was 45% (21 patients). The best response, as determined by the investigator, was complete response (CR) for 3 (7%) patients, partial response (PR) for 10 (21%) patients, and stable disease (SD) for 12 (26%) patients. 19 (41%) patients had a best response of PD.

Patients with Lymphoma

Among the 27 patients with lymphoma, the ORR was 40% (11 patients) and the CBR was 62% (15 patients). The best response, as determined by the investigator, was CR for 3 (11%) patients, PR for 8 (30%) patients, and SD for 6 (22%) patients. 10 (37%) patients had a best response of PD.

Although the sample size is small, the ORR and CBR were higher among those patients in the LYM60 mg/m$^2$/30 min cohort and 100% (3/3)) than in the L80 mg/m$^2$/45 min cohort.

Signals of efficacy were observed among the 10 patients with HL, with 70% (7 patients) having a response from SD to CR. One patient who achieved a CR was previously primary refractory, and had displayed no response to chemo-radiotherapy, brentuximab vedotin or immune checkpoint inhibitors, and had never been the recipient of autologous stem cell transplantation owing to their primary disease.

Upon achieving CR, this patient was consolidated by receiving an allogeneic haemopoietic stem cell (haplo-transplant) and is graft versus host disease free (GvHD)-free (>20 months) following the last tinostamustine dose.

Patients with Multiple Myeloma (MM)

Among the 19 patients with MM, the ORR was 11% (2 patients) and the CBR was 42% (6 patients). The best response, as determined by the investigator, was CR for 0 patients, PR for 2 (11%) patients, and SD for 6 (31%) patients. 9 (47%) patients had a best response of PD. The CBR was the same in each MM dose cohort.

10 (52%) out of 19 patients with MM had refractory disease or were refractory to previous therapies. Median number of previous therapy lines was 6 (2-13) and median age was 72 (54-83).

Some patients with MM showed a rise in peripheral blood light chain values before day 21 indicating an earlier disease recovery. This would indicate that a once every 3-week schedule is not optimal in controlling MM disease and an administration once every 2 weeks may be more appropriate.

Summary and Conclusions

Safety

The principle toxicities associated with tinostamustine have been hematologic abnormalities, primarily thrombocytopenia, neutropenia, anaemia. Across all cohorts, a dose relationship was apparent with regard to the incidence of this toxicity, with the incidence increasing with increasing dose and shortening infusion time. Haematological nadir occurs between day 17 and 23. Thrombocytopenia was determined as the DLT at a dose of 120 mg/m$^2$ in lymphoma cohort. In multiple myeloma subpopulation, the decline in platelet count was associated with a prolonged recovery of thrombocytes exceeding the treatment cycle and was observed in patients at 100 mg/m$^2$.

PK and Infusion Time:

The PK of tinostamustine over a dose range of 20 to 120 mg/m$^2$ given over 60 minutes infusion time is linear. Time to $C_{max}$ is achieved between 45 and 60 minutes for the 60 minutes. Decline from peak concentration occurred in a bi-phasic manner.

Evaluation of shorter infusion time, especially a 30 minute infusion showed that the $C_{max}$ was doubled for the same AUC. The $C_{max}$ was variable in particular in the 60 mg/m$^2$/30-minute infusion cohort, where the standard deviation was the largest at 1416 ng/mL. The sponsor stopped evaluation of shorter infusion time and decided to use 60 minutes infusion for further development.

Thrombocytopenia and RP2D

Platelet count at baseline was determined as the sole factor to predict grade 3 or 4 thrombocytopenia. Consequently, the recommended doses of tinostamustine depend on the platelet count at treatment initiation.

Dosing Schedule

Lymphoma: administration on day 1 in 21-day cycle provided to be well tolerated and efficacious in Lymphoma patients.

Multiple Myeloma: some patients with multiple myeloma showed a rise in peripheral blood light chain values before day 21 indicating an earlier disease recovery. This indicates that a once every 3-week schedule is not optimal in controlling MM disease. Therefore, administration on day 1 and day 15 in a 28-day cycle is recommended. It was also considered that the overall development strategy for multiple myeloma does not include studies as a single agent in multi-refractory disease, but rather would continue with a safe and likely effective dose for combination studies with other approved agents such as a proteasome inhibitor, a CD 38 antibody or a Bcl-2 modifying agent.

Selection of the Recommended Phase 2 Dose

Recommended Dose and Schedule of Tinostamustine for the Treatment of Relapse Refractory Lymphoma Patients 1. Baseline platelet count 200×10$^9$/L: the starting tinostamustine dose is 100 mg/m$^2$ over 60 minutes infusion. Administration on day 1 of 21-day cycle. If the platelet count decreases to <50×10$^9$/L, the dose should be reduced to 80 mg/m$^2$ and maintained for subsequent treatment cycles.

2. Baseline platelet count<200×10$^9$/L>100×10$^9$/L: the starting tinostamustine dose is 80 mg/m$^2$ over 60 minutes infusion. Administration day 1 of 21-day cycle. If the platelet count decreases to <50×10$^9$/L the dose should be reduced to 60 mg/m$^2$ and maintained for subsequent treatment cycles.

3. Baseline platelet count 100×10$^9$/L: the starting tinostamustine dose is 50 mg/m$^2$ over 60 minutes infusion. Administration day 1 of 21-day cycle. If the platelet count decreases to <50×10$^9$/L, the dose should be reduced to 40 mg/m$^2$ and maintained for subsequent treatment cycles.

Recommended Dose and Schedule of Tinostamustine for the Treatment of Relapse Refractory Multiple Myeloma Patients 1. Baseline platelet count>100×10$^9$/L: the starting tinostamustine dose is 60 mg/m$^2$ over 60 minutes infusion. Administration day 1 and day 15 of 28-day cycle. If the platelet count decreases to <50×10$^9$/L, the dose should be reduced to 50 mg/m$^2$ and maintained for subsequent treatment cycles.

2. Baseline platelet count 100×10$^9$/L: the starting tinostamustine dose is 50 mg/m$^2$ over 60 minutes infusion. Administration day 1 and day 15 of 28-day cycle. If the platelet count decreases to <50×10$^9$/L, the dose should be reduced to 40 mg/m$^2$ and maintained for subsequent treatment cycles.

The invention claimed is:

1. A method of treating lymphoma or a T-cell malignant disease in a patient having said lymphoma or said T-cell malignant disease, said method comprising administering to the patient an amount of tinostamustine or a pharmaceutically acceptable salt thereof, wherein the amount is:
   (i) if the patient's initial platelet count is equal to or above 200×10$^9$/L, a first amount of tinostamustine or pharmaceutically acceptable salt thereof of 95 mg/m$^2$ or greater, based on free tinostamustine and the patient's body surface area; and
   (ii) if the patient's initial platelet count is equal to or below 100×10$^9$/L, a second amount of tinostamustine or pharmaceutically acceptable salt thereof of 54 mg/m$^2$ or lower; and
   (iii) if the patient's initial platelet count is between 100×10$^9$/L and 200×10$^9$/L, a third amount of tinostamustine or pharmaceutically acceptable salt thereof of 75-85 mg/m$^2$ is administered.

2. The method according to claim 1 wherein the tinostamustine or pharmaceutically acceptable salt thereof is administered over 4 to 8 treatment cycles.

3. The method according to claim 2 wherein the tinostamustine or pharmaceutically acceptable salt thereof is administered on day 1 of a 21-day treatment cycle.

4. The method according to claim 2, comprising:
   (a) determining the patient's platelet count before each subsequent treatment cycle; and
   administering to the patient an amount of tinostamustine or pharmaceutically acceptable salt thereof, based on the results of the patient's platelet count before said each subsequent treatment cycle, wherein the amount is:
   (i) 95 mg/m$^2$ or greater, based on free tinostamustine and the patient's body surface area, if the patient's initial platelet count was greater than or equal to 200×10$^9$/L and the patient's platelet count before the subsequent treatment cycle is greater than or equal to 50×10$^9$/L;
   (ii) 84 mg/m$^2$ or lower, based on free tinostamustine and the patient's body surface area, if the patient's initial platelet count was greater than or equal to 200×10$^9$/L and the patient's platelet count before the subsequent treatment cycle is less than 50×10$^9$/L;
   (iii) 75-85 mg/m$^2$, based on free tinostamustine and the patient's body surface area, if the patient's initial platelet count is between 100×10$^9$/L and 200×10$^9$/L and the patient's platelet count before the subsequent treatment cycle is greater than or equal to 50×10$^9$/L;

(iv) 55-65 mg/m$^2$, based on free tinostamustine and the patient's body surface area, if the patient's initial platelet count is between 100×10$^9$/L and 200×10$^9$/L and the patient's platelet count before the subsequent treatment cycle is less than 50×10$^9$/L;

(v) 54 mg/m$^2$ or lower, based on free tinostamustine and the patient's body surface area, if the patient's initial platelet count was less than 100×10$^9$/L and the patient's platelet count before the subsequent treatment cycle is greater than or equal to 50×10$^9$/L; or, (vi) 44 mg/m$^2$ or lower, based on free tinostamustine and the patient's body surface area, if the patient's initial platelet count was less than 100×10$^9$/L and the patient's platelet count before the subsequent treatment cycle is less than 50×10$^9$/L.

5. A method of treating lymphoma or a T-cell malignant disease in a patient having said lymphoma or said T-cell malignant disease, said method comprising administering to the patient an amount of tinostamustine or a pharmaceutically acceptable salt thereof, wherein the amount is:

(a) 95 mg/m$^2$ or greater based on free tinostamustine and the patient's body surface area, if the patient has a baseline platelet count of greater than or equal to 200×10$^9$/L;

(b) 75-85 mg/m$^2$ based on free tinostamustine and the patient's body surface area, if the patient has a baseline platelet count of between 100×10$^9$/L and 200×10$^9$/L; or (c) 54 mg/m$^2$ or lower based on free tinostamustine and the patient's body surface area, if the patient has a baseline platelet count of less than or equal to 100×10$^9$/L.

6. The method according to claim 1, wherein the tinostamustine or pharmaceutically acceptable salt thereof is administered intravenously.

7. The method according to claim 6, wherein the tinostamustine or pharmaceutically acceptable salt thereof is administered over 45-75 minutes.

8. The method according to claim 1, wherein tinostamustine is in the form of a pharmaceutically acceptable salt selected from the group of hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, oxalate, succinate, fumarate, tartrate, tosylate, mandelate, salicylate, lactate, p-toluenesulfonate, naphthalenesulfonate or acetate.

9. The method according to claim 1, wherein tinostamustine is in the form of the free compound.

10. The method according to claim 1, wherein the lymphoma is relapsed or refractory lymphoma.

11. The method according to claim 1, wherein the lymphoma is:

Hodgkin lymphoma; or non-Hodgkin lymphoma comprising NK/T-cell lymphoma, peripheral T-cell lymphoma (PTCL), cutaneous T-cell lymphoma (CTCL), or anaplastic large cell lymphoma (ALCL).

12. The method according to claim 1, wherein the T-cell malignant disease is T-cell-prolymphocytic leukemia (T-PLL).

13. The method according to claim 1, wherein the tinostamustine or the pharmaceutically acceptable salt thereof is used as a monotherapy.

14. The method according to claim 1, wherein the tinostamustine or the pharmaceutically acceptable salt thereof is used in combination with one or more other compounds or therapies.

15. The method according to claim 14, wherein the tinostamustine or the pharmaceutically acceptable salt and the one or more other compounds or therapies are administered concurrently, sequentially or separately.

16. The method according to claim 14, wherein the one or more other compounds are selected from glucocorticoids, dexamethasone, fluocinolone acetonide and prednisone.

17. The method according to claim 14, wherein the one or more other compounds are selected from proteasome inhibitors, bortezomib, carfilzomib, marizomib, delanzomib (CEP-18770), oprozomib (ONX 0912), ixazomib (MLN-9708), and LU-102.

18. The method according to claim 14, wherein the one more other therapies comprises radiotherapy.

* * * * *

UNITED STATES PATENT AND TRADEMARK OFFICE
CERTIFICATE OF CORRECTION

PATENT NO. : 12,377,076 B2
APPLICATION NO. : 17/414797
DATED : August 5, 2025
INVENTOR(S) : Katarina Hilgier et al.

Page 1 of 1

It is certified that error appears in the above-identified patent and that said Letters Patent is hereby corrected as shown below:

In the Claims

At Column 30, Claim number 1, Line number 37, delete "is administered"

Signed and Sealed this
Sixteenth Day of September, 2025

Coke Morgan Stewart
*Acting Director of the United States Patent and Trademark Office*